US012365735B2

(12) United States Patent
Gulla et al.

(10) Patent No.: US 12,365,735 B2
(45) Date of Patent: Jul. 22, 2025

(54) ANTI-KLRG1 ANTIBODIES

(71) Applicant: THE BRIGHAM AND WOMEN'S HOSPITAL, INC., Boston, MA (US)

(72) Inventors: Stefano V Gulla, Medford, MA (US); Kenneth Evan Thompson, Arlington, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1076 days.

(21) Appl. No.: 17/285,793

(22) PCT Filed: Sep. 6, 2019

(86) PCT No.: PCT/US2019/050110
§ 371 (c)(1),
(2) Date: Apr. 15, 2021

(87) PCT Pub. No.: WO2020/060781
PCT Pub. Date: Mar. 26, 2020

(65) Prior Publication Data
US 2021/0347899 A1    Nov. 11, 2021

Related U.S. Application Data

(60) Provisional application No. 62/732,329, filed on Sep. 17, 2018.

(51) Int. Cl.
C07K 16/28   (2006.01)
A61K 39/395  (2006.01)

(52) U.S. Cl.
CPC ...... C07K 16/2851 (2013.01); C07K 2317/24 (2013.01); C07K 2317/567 (2013.01); C07K 2317/76 (2013.01)

(58) Field of Classification Search
None
See application file for complete search history.

(56) References Cited

U.S. PATENT DOCUMENTS

| | | | |
|---|---|---|---|
| 5,624,821 A | 4/1997 | Winter et al. | |
| 6,737,056 B1 | 5/2004 | Presta | |
| 7,597,889 B1 | 10/2009 | Armour et al. | |
| 8,613,926 B2 | 12/2013 | Kjaergaard et al. | |
| 8,846,045 B2 | 9/2014 | Kjaergaard et al. | |
| 8,969,526 B2 | 3/2015 | Bachner et al. | |
| 9,127,061 B2 | 9/2015 | Zhang et al. | |
| 9,200,079 B2 | 12/2015 | Chamberlain et al. | |
| 9,803,023 B2 | 10/2017 | Chamberlain et al. | |
| 9,988,459 B2 | 6/2018 | Coyle et al. | |
| 10,053,513 B2 | 8/2018 | McCarthy et al. | |
| 10,301,390 B2 | 5/2019 | Coyle et al. | |
| 10,577,422 B2 | 3/2020 | Shah et al. | |
| 2006/0134709 A1 | 6/2006 | Stavenhagen et al. | |
| 2010/0166740 A1 | 7/2010 | Endl et al. | |
| 2014/0170140 A1 | 6/2014 | Bennett et al. | |
| 2014/0221620 A1 | 8/2014 | Zhang et al. | |
| 2016/0194389 A1 | 7/2016 | Regula et al. | |
| 2017/0107297 A1 | 4/2017 | Chang et al. | |
| 2017/0190766 A1 | 7/2017 | Perlroth et al. | |
| 2018/0273622 A1 | 9/2018 | Tan et al. | |
| 2018/0334496 A1 | 11/2018 | Perlroth et al. | |
| 2019/0211113 A1 | 7/2019 | Amann et al. | |
| 2019/0336615 A1 | 11/2019 | Thompson et al. | |
| 2024/0174754 A1 | 5/2024 | Gulla et al. | |

FOREIGN PATENT DOCUMENTS

| | | |
|---|---|---|
| CN | 101663323 | 3/2010 |
| CN | 103347896 | 10/2013 |
| EP | 1075496 | 2/2001 |
| EP | 1817340 | 8/2007 |
| EP | 2250279 | 11/2010 |
| EP | 2325206 | 5/2011 |
| EP | 2325207 | 5/2011 |
| JP | 2017-518958 | 7/2017 |
| WO | WO 1999058572 | 11/1999 |
| WO | WO 2020210512 | 10/2000 |
| WO | WO 2006047350 | 5/2006 |
| WO | WO 2006053301 | 5/2006 |
| WO | WO 2006076594 | 7/2006 |
| WO | WO 2009100309 | 8/2009 |
| WO | WO 2011016238 | 2/2011 |
| WO | WO 2016009487 | 1/2016 |
| WO | WO 2017152102 | 9/2017 |
| WO | 2017210523 A1 | 12/2017 |
| WO | 2018053264 A2 | 3/2018 |
| WO | WO 2018237341 | 12/2018 |
| WO | WO 2019169229 | 9/2019 |

(Continued)

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Research Commmunications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Greenberg, S.A., et al., Abstract LB-301, "Inhibition of the co-inhibitory receptor KLRG1 reduces murine 4T1 breast cancer metastasis and MC38 colon cancer primary tumor growth and mortality," Cancer Research, Jul. 1, 2018, vol. 78, No. 13 Supplement, pp. LB-301-LB-301 (whole document).

(Continued)

Primary Examiner — Christine J Saoud
Assistant Examiner — Jon M Lockard
(74) Attorney, Agent, or Firm — Fish & Richardson P.C.

(57) ABSTRACT

The invention relates to antibodies, or antigen-binding fragments thereof, that specifically binds to killer cell lectin-like receptor G1 (KLRG1). Such antibodies, or antigen-binding fragments thereof, are useful for various therapeutic or diagnostic purposes including treatment of cancers and to increase the effectiveness of vaccines.

16 Claims, 3 Drawing Sheets
Specification includes a Sequence Listing.

(56) References Cited

FOREIGN PATENT DOCUMENTS

WO    WO 2020060781    3/2020

OTHER PUBLICATIONS

Armour et al., "Recombinant human IgG molecules lacking Fcγ receptor I binding and monocyte triggering activities," European Journal of Immunology, Aug. 1999, 29(8):2613-2624.

CN Office Action in Chinese Appln. No. 201980060735.4, mailed on May 31, 2024, 9 pages (with English translation).

CN Office Action in Chinese Appln. No. 201980060735.4, mailed on Oct. 31, 2023, 16 pages (with English translation).

Grundenmann et al., "The NK receptor KLRG1 is dispensable for virus-induced NK and CD8⁺ T-cell differentiation and function in vivo," European Journal of Immunology, May 2010, 40(5):1303-1314.

Henson et al., "KLRG1—more than a marker for T cell senescence," Age, Dec. 2009, 31(4):285-291.

Idusogie et al., "Engineered Antibodies with Increased Activity to Recruit Complement," Journal of Immunology, Feb. 2001, 166(4):2571-2575.

JP Office Action in Japanese Appln No. 2021-539334, mailed on Aug. 22, 2023, 10 pages (with English translation).

JP Office Action in Japanese Appln No. 2021-539334, mailed on Jan. 25, 2024, 6 pages (with English translation).

JP Office Action in Japanese Appln No. 2021-539334, mailed on Mar. 29, 2024, 5 pages (with English translation).

Lu et al., "Deamidation and isomerization liability analysis of 131 clinical-stage antibodies," MAbs, Jan. 2019, 11(1):45-57.

Lund et al., "Human FcγRI and FcγRII interact with distinct but overlapping sites on human IgG," Journal of Immunology, Oct. 1991, 147(8):2657-2662.

Oganesyan et al., "Structural characterization of a human Fc fragment engineered for lack of effector functions," Acta Crystallographica Section D, Jun. 2008, D64(6):700-704.

PCT International Preliminary Report on Patentability in International Appln. No. PCT/US2019/050110, mailed on Mar. 9, 2021, 6 pages.

PCT International Preliminary Report on Patentability in International Appln. No. PCT/US2022/021945, mailed on Sep. 19, 2023, 7 pages.

PCT International Search Report and Written Opinion in International Appln. No. PCT/2022/021945, mailed on Jul. 5, 2022, 12 pages.

Shields et al., "High Resolution Mapping of the Binding Site on Human IgG1 for FcγRI, FcγRII, FcγRIII, and FcRn and Design of IgG1 Variants with Improved Binding to the FcγR," Journal of Biological Chemistry, Mar. 2001, 276(9):6591-6604.

SG Office Action in Singaporean Appln. No. 11202102114U, mailed on Nov. 12, 2024, 8 pages.

Supplementary European Search Report for European Patent Application No. 19862063.5, dated May 10, 2022.

International Search Report and Written Opinion for PCT/2019/050110 mailed on Jan. 29, 2020.

\* cited by examiner

ANTI-KLRG1 ANTIBODIES

TECHNICAL FIELD

The technical field relates to inhibition of the lymphocyte co-inhibitory receptor Killer Cell Lectin-Like Receptor Subfamily G Member 1 (KLRG1).

BACKGROUND

Lymphocyte co-inhibitory receptors modulate the action of the adaptive immune system, for example T cells and NK cells, in response to activating signals such as antigenic peptides in the context of the major histocompatibility complex (MIIC) binding to the T cell receptor (TCR). Co-inhibitory receptors include PD-1, LAG-3, TIM-3, and CTLA4. The action of co-inhibitory receptors is generally carried out by binding of a ligand to the extracellular domain of the co-inhibitory receptor followed by recruitment of intracellular phosphatases by an immunoreceptor tyrosine-based inhibition motif (ITIM) located in the intracellular domain of the co-inhibitory receptor. The action of co-inhibitory receptors is generally to dampen the immune response of TCR engagement. In recent years it has been shown that agents that block the activity of co-inhibitory receptors can be used to as efficacious treatments for cancer and infectious diseases.

Killer cell lectin-like receptor G1 (KLRG1) is a type II transmembrane protein acting as co-inhibitory receptor by modulating the activity of T and NK cells. Its extracellular portion contains a C-type lectin domain whose known ligands are cadherins and its intracellular portion contains an immunoreceptor tyrosine-based inhibitory motif (ITIM) domain responsible for co-inhibition of T cell receptor (TCR) mediated signaling. KLRG1 ligands can be E-cadherin, N-cadherin, R-cadherin, or a combination thereof.

The receptor killer cell lectin-like receptor G1 (KLRG1) is expressed on T and NK cells which binds to ligands on epithelial and mesenchymal cells. The ligand for KLRG1 have been described to be E-cadherin, N-cadherin and R-cadherin.

In humans, KLRG1 expression is confined to cells of the immune systems and specifically to CD8 positive T cells, NK cells and to a lesser extent to CD4 positive T cells. KLRG1 expression has been associated with the late differentiated phenotype. As antigen specific T cells differentiate they acquire increased expression of cytotoxic molecules and therefore have increased cytotoxic potential. The biological function of KLRG1 is to inhibit cytotoxicity and proliferation of these T cells. In cancer and infectious disease, it has been shown beneficial to restore T cell activity.

In general, a need exists to provide safe and effective therapeutic methods for cancer or infectious diseases. Modulation of the cytotoxic (or CD8+) T and NK cell activation involved in these disorders can be accomplished by manipulation of the KLRG1 pathway.

SUMMARY

The present disclosure provides characterization of novel antibodies, or antigen binding fragments thereof, that bind the extracellular domain (ECD) of KLRG1 and inhibit its interaction with ligands E-cadherin, N-cadherin and R-cadherin. The antibodies here described have been derived by mouse hybridoma technology and can be humanized by grafting their complementary determining regions (CDRs) into a human framework. The disclosure also provides antibodies or binding fragments that modulate (e.g., activate) CD8+ cytotoxic T and NK cells and do so by modulating (e.g., neutralizing) the interaction between KLRG1 and its ligands. The antibodies here described can be used as effective therapeutic agents for treatment of cancer either as monotherapy, or in combination with other immunotherapy agents (such as anti-PD-1 antibodies, anti-PD-L1 antibodies, or anti-CTLA4 antibodies), or in combination with chemotherapy agents, or cancer vaccines. The antibodies here described can be used as effective treatments for infectious diseases or to enhance the effectiveness of vaccines against infectious diseases.

Nonlimiting illustrative embodiments of the antibodies are referred to as ABC_HG1N01, ABC_HG1N02, ABC_HG1N07, ABC_G1N01, ABC_G1N02, ABC_G1N03, ABC_G1N04, ABC_G1N05, ABC_G1N06, ABC_G1N07, or ABC_G1N08. Other embodiments comprise a $V_H$ and/or $V_L$ domain of the Fv fragment of ABC_HG1N01, ABC_HG1N02, ABC_HG1N07, ABC_G1N01, ABC_G1N02, ABC_G1N03, ABC_G1N04, ABC_G1N05, ABC_G1N06, ABC_G1N07, or ABC_G1N08. Further embodiments comprise one or more CDRs of any of these $V_H$ and $V_L$ domains. Other embodiments comprise an H3 fragment of the $V_H$ domain of ABC_HG1N01, ABC_HG1N02, ABC_HG1N07, ABC_G1N01, ABC_G1N02, ABC_G1N03, ABC_G1N04, ABC_G1N05, ABC_G1N06, ABC_G1N07, and ABC_G1N08.

The disclosure also provides compositions comprising KLRG1 antibodies, and their use in methods of modulating immune response, including methods of treating humans or animals. In particular embodiments, anti-KLRG1 antibodies are used to treat or prevent cancer by virtue of activating CD8+ cytotoxic T and NK cells. Disorders susceptible to treatment with compositions of the invention include but are not limited cancer and infectious diseases.

Additionally, anti-KLRG1 antibodies may be used diagnostically to detect KLRG1 or its fragments in a biological sample. The amount of KLRG1 detected may be correlated with the expression level of KLRG1, which, in turn, is correlated with the activation status of lymphocytes (e.g., cytotoxic T cells or Natural Killer cells) in the subject.

The disclosure also provides isolated nucleic acids, which comprise a sequence encoding a $V_H$ or $V_L$ domain from the Fv fragment of ABC_HG1N01, ABC_HG1N02, ABC_HG1N07, ABC_G1N01, ABC_G1N02, ABC_G1N03, ABC_G1N04, ABC_G1N05, ABC_G1N06, ABC_G1N07, and ABC_G1N08. Also provided are isolated nucleic acids, which comprise a sequence encoding one or more CDRs from any of the presently disclosed $V_H$ and $V_L$ domains. The disclosure also provides vectors and host cells comprising such nucleic acids.

The disclosure further provides a method of producing new $V_H$ and $V_L$ domains and/or functional antibodies comprising all or a portion of such domains derived from the $V_H$ or $V_L$ domains of ABC_HG1N01, ABC_HG1N02, ABC_HG1N07, ABC_G1N01, ABC_G1N02, ABC_G1N03, ABC_G1N04, ABC_G1N05, ABC_G1N06, ABC_G1N07, and ABC_G1N08.

Additional aspects of the disclosure will be set forth in part in the description which follows, and in part will be obvious from the description, or may be learned by practicing the invention. The invention is set forth and particularly pointed out in the appended claims, and the present disclosure should not be construed as limiting the scope of the claims in any way. The following detailed description includes exemplary representations of various embodiments of the invention, which are not restrictive of the invention, as claimed. The accompanying figures constitute a part of this specification and, together with the description, serve only to illustrate various embodiments and not limit the invention. Citation of references is not an admission that these references are prior art to the invention.

DETAILED DESCRIPTION

Definitions

Figure 1:
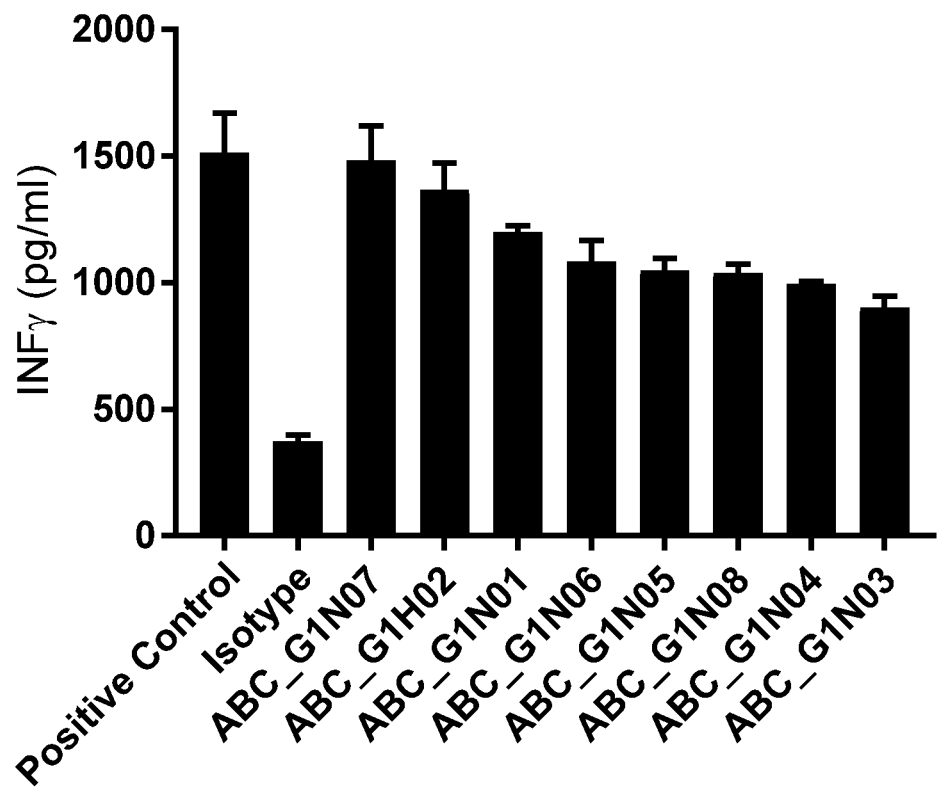
FIG. 1 shows results of an interferon-gamma (IFNγ) secretion assay demonstrating that anti-KLRG1 antibodies activate CD8+ human T cells.

The term "antibody," as used in this disclosure, refers to an immunoglobulin or a fragment or a derivative thereof, and encompasses any polypeptide comprising an antigen-binding site, regardless whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')$_2$, Fv, scFv, Fd, dAb, and other antibody fragments that retain antigen-binding function, i.e., the ability to bind KLRG1 specifically. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances where an antigen is large, the antigen-binding domain may only bind to a part of the antigen. A portion of the antigen molecule that is responsible for specific interactions with the antigen-binding domain is referred to as "epitope" or "antigenic determinant."

An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

The term "repertoire" refers to a genetically diverse collection of nucleotides derived wholly or partially from sequences that encode expressed immunoglobulins. The sequences are generated by in vivo rearrangement of, e.g., V, D, and J segments for H chains and, e.g., V and J segment for L chains. Alternatively, the sequences may be generated from a cell line by in vitro stimulation, in response to which the rearrangement occurs. Alternatively, part or all of the sequences may be obtained by combining, e.g., unrearranged V segments with D and J segments, by nucleotide synthesis, randomised mutagenesis, and other methods, e.g., as disclosed in U.S. Pat. No. 5,565,332.

The terms "specific interaction" and "specific binding" refer to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ M$^{-1}$ or more preferably higher than $10^8$ M$^{-1}$. If necessary, non-specific binding can be reduced without substantially affecting specific binding by varying the binding conditions. The appropriate binding conditions such as concentration of antibodies, ionic strength of the solution, temperature, time allowed for binding, concentration of a blocking agent (e.g., serum albumin, milk casein), etc., may be optimized by a skilled artisan using routine techniques.

The phrase "substantially as set out" means that the relevant CDR, $V_H$, or $V_L$ domain of the invention will be either identical to, or have only insubstantial differences in the specified regions (e.g., a CDR) from the sequence of which is set out. Insubstantial differences include minor amino acid changes, such as substitutions of 1 or 2 out of any 5 amino acids in the sequence of a specified region.

The term "KLRG1 activity" refers to one or more lymphocyte co-inhibitory activities associated with KLRG1. For example, KLRG1 activity may mean modulation of cytotoxic T and NK cell activation.

The term "modulate," and its cognates refer to a reduction or an increase in the activity of KLRG1 associated with activation of T cells and NK cells due to its interaction with an anti-KLRG1 antibody, wherein the reduction or increase is relative to the activity of KLRG1 in the absence of the same antibody. A reduction or an increase in activity is preferably at least about 10%, 20%, 30%, 40%, 50%, 60%, 70%, 80%, 90%, or more. When KLRG1 activity is reduced, the terms "modulatory" and "modulate" are interchangeable with the terms "inhibitory" and "inhibit." When KLRG1 activity is increased, the terms "modulatory" and "modulate" are interchangeable with the terms "activating" and "activate." The activity of KLRG1 can be determined quantitatively using T cell and NK cell activation assays such as those described in Example 6.

The terms "treatment" and "therapeutic method" refer to both therapeutic treatment and prophylactic/preventative measures. Those in need of treatment may include individuals already having a particular medical disorder as well as those who may ultimately acquire the disorder (i.e., those needing preventative measures).

The term "effective amount" refers to a dosage or amount that is sufficient to reduce the activity of KLRG1 to result in amelioration of symptoms in a patient or to achieve a desired biological outcome, e.g., reduced activity of KLRG1, modulation of lymphocyte co-inhibition response, increased activation of cytotoxic T and NK cells, or increased release of IFNγ by cytotoxic T cells or NK cells.

The term "isolated" refers to a molecule that is substantially free of its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

Anti-KLRG1 Antibodies

The disclosure provides anti-KLRG1 antibodies that comprise novel antigen-binding fragments.

In general, antibodies can be made, for example, using traditional hybridoma techniques (Kohler and Milstein (1975) Nature, 256: 495-499), recombinant DNA methods (U.S. Pat. No. 4,816,567), or phage display performed with antibody libraries (Clackson et al. (1991) Nature, 352: 624-628; Marks et al. (1991) J. Mol. Biol., 222: 581-597). For other antibody production techniques, see also Antibodies: A Laboratory Manual, eds. Harlow et al., Cold Spring Harbor Laboratory, 1988. The invention is not limited to any particular source, species of origin, or method of production.

Intact antibodies, also known as immunoglobulins, are typically tetrameric glycosylated proteins composed of two light (L) chains of approximately 25 kDa each and two heavy (H) chains of approximately 50 kDa each. Two types of light chain, designated as the λ chain and the κ chain, are found in antibodies. Depending on the amino acid sequence of the constant domain of heavy chains, immunoglobulins can be assigned to five major classes: A, D, E, G, and M, and several of these may be further divided into subclasses (isotypes), e.g., IgG1, IgG2, IgG3, IgG4, IgA1, and IgA2.

The subunit structures and three-dimensional configurations of different classes of immunoglobulins are well known in the art. For a review of antibody structure, see Harlow et al., supra. Briefly, each light chain is composed of an N-terminal variable domain ($V_L$) and a constant domain ($C_L$). Each heavy chain is composed of an N-terminal variable domain ($V_H$), three or four constant domains ($C_H$), and a hinge region. The $C_H$ domain most proximal to $V_H$ is designated as $C_H1$. The $V_H$ and $V_L$ domains consist of four regions of relatively conserved sequence called framework regions (FR1, FR2, FR3, and FR4), which form a scaffold for three regions of hypervariable sequence called complementarity determining regions (CDRs). The CDRs contain most of the residues responsible for specific interactions with the antigen. The three CDRs are referred to as CDR1, CDR2, and CDR3. CDR constituents on the heavy chain are referred to as H1, H2, and H3, while CDR constituents on the light chain are referred to as L1, L2, and L3, accordingly. CDR3 and, particularly H3, are the greatest source of molecular diversity within the antigen-binding domain. H3, for example, can be as short as two amino acid residues or greater than 26.

The Fab fragment (Fragment antigen-binding) consists of the $V_H$-$C_H1$ and $V_L$-$C_L$ domains covalently linked by a disulfide bond between the constant regions. To overcome the tendency of non-covalently linked $V_H$ and $V_L$ domains in the Fv to dissociate when co-expressed in a host cell, a so-called single chain (sc) Fv fragment (scFv) can be constructed. In a scFv, a flexible and adequately long polypeptide links either the C-terminus of the $V_H$ to the N-terminus of the $V_L$ or the C-terminus of the $V_L$ to the N-terminus of the $V_H$. Most commonly, a 15-residue (Gly$_4$Ser)$_3$ peptide is used as a linker but other linkers are also known in the art.

Antibody diversity is a result of combinatorial assembly of multiple germline genes encoding variable regions and a variety of somatic events. The somatic events include recombination of variable gene segments with diversity (D) and joining (J) gene segments to make a complete $V_H$ region and the recombination of variable and joining gene segments to make a complete $V_L$ region. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation.

Based on the estimated number of germline gene segments, the random recombination of these segments, and random $V_H$-$V_L$ pairing, up to $1.6 \times 10^7$ different antibodies could be produced (Fundamental Immunology, 3rd ed., ed. Paul, Raven Press, New York, N.Y., 1993). When other processes which contribute to antibody diversity (such as somatic mutation) are taken into account, it is thought that upwards of $1 \times 10^{10}$ different antibodies could be potentially generated (Immunoglobulin Genes, 2nd ed., eds. Jonio et al., Academic Press, San Diego, Calif., 1995). Because of the many processes involved in antibody diversity, it is highly unlikely that independently generated antibodies will have identical amino acid sequences in the CDRs.

The disclosure provides novel CDRs derived from human immunoglobulin gene libraries. The structure for carrying a CDR will generally be an antibody heavy or light chain or a portion thereof, in which the CDR is located at a location corresponding to the CDR of naturally occurring $V_H$ and $V_L$. The structures and locations of immunoglobulin variable domains may be determined, for example, as described in Kabat et al., Sequences of Proteins of Immunological Interest, No. 91-3242, National Institutes of Health Publications, Bethesda, Md., 1991.

Amino acid sequences of $V_H$ and $V_L$ domains of humanized anti-KLRG1 antibodies are set forth in the Sequence Listing and are enumerated as listed in Tables 1.

TABLE 1

Amino acid sequences of variable regions for humanized anti-KLRG1 antibodies

| SEQ ID NO. | mAb | $V_H$/$V_L$ | Amino Acid Sequence |
|---|---|---|---|
| SEQ ID NO: 1 | ABC_HG1N01 | $V_H$ | QVILKESGPGLVKPTQTLTLTCTFSGF SLTTFGMGIGWIRQPPGKALEWLAHIW WNDDKSYNSALKSRLTISKDTSKNQVV LTMTNMDPVDTATYYCARTIYYGNYLT FYAMEHWGQGTTVTVSS |
| SEQ ID NO: 2 | | $V_L$ | DILMTQSPLSLPVTPGEPASISCRSSQ NIVHSNGNTYLEWYLQKPGQSPRLLIY KVSNRFSGVPDRFSGSGSGTDFTLKIS RVEAEDVGVYYCFQGSHVPPTFGAGTK LELKRTV |
| SEQ ID NO: 3 | ABC_HG1N02 | $V_H$ | QVTLKESGPGLVKPTQTLTLTCTFSGF SLSTFGMGVGWIRQPPGKALEWLAHIW WDDDKWYELALKSRLTISKDSSKNQVV LTMTNMDPVDTATYYCARVIYYGSRSA YYSMDYWGPGTTVTVSS |
| SEQ ID NO: 4 | | $V_L$ | DILMTQSPLSLPVTPGEPASISCKSSQ SIVHSNGHTYLEWYLQKPGQSPRLLIY KVSNRFSGVPDRFSGSGSGTDFTLKIS RVEAEDVGVYYCFQGSHVPVTFGAGTK LELKRTV |
| SEQ ID NO: 5 | ABC_HG1N07 | $V_H$ | QVQLVESGGGLVKPGGSLRLSCAASGF TFRNYAMSWIRQTPGKGLEWVATISES GNYNNYPDNVKGRLTISRDNAKNSLYL QMNSLKAEDTAVYYCVRDDWEGRAMDY WGQGTTVTVSS |
| SEQ ID NO: 6 | | $V_L$ | DIQMTQSPSSLSASVGDRVTITCRASR DIGSSLNWYQQKPGGAPKRLIYATSSL DSGVPKRFSGSGSGTDFTLTISSLQSE DFATYYCLQYASSPWTFGQGTKVEIKR TV |

Particular nonlimiting illustrative embodiments of the antibodies are referred to as ABC_HG1N01, ABC_HG1N02, and ABC_HG1N07. Amino acid sequences of CDRs within the $V_H$ and $V_L$ domains of the illustrative embodiments are set forth in the Sequence Listing and are enumerated as listed in Table 2.

TABLE 2

CDR amino acid sequences for humanized anti-KLRG1 antibodies

| SEQ ID NO. | mAb | CDR | Amino Acid Sequence |
|---|---|---|---|
| SEQ ID NO: 7 | ABC_HG1N01 | CDR-H1 | GFSLTTFGM |
| SEQ ID NO: 8 | | CDR-H2 | WWNDD |
| SEQ ID NO: 9 | | CDR-H3 | TIYYGNYLTFYAMEH |
| SEQ ID NO: 10 | | CDR-L1 | RSSQNIVHSNGNTYLE |
| SEQ ID NO: 11 | | CDR-L2 | KVSNRFS |
| SEQ ID NO: 12 | | CDR-L3 | FQGSHVPPT |
| SEQ ID NO: 13 | ABC_HG1N02 | CDR-H1 | GFSLSTFGM |
| SEQ ID NO: 14 | | CDR-H2 | WWDDD |
| SEQ ID NO: 15 | | CDR-H3 | VIYYGSRSAYYSMDY |

TABLE 2-continued

CDR amino acid sequences for humanized anti-KLRG1 antibodies

| SEQ ID NO. | mAb | CDR | Amino Acid Sequence |
|---|---|---|---|
| SEQ ID NO: 16 | | CDR-L1 | KSSQSIVHSNGHTYLE |
| SEQ ID NO: 17 | | CDR-L2 | KVSNRFS |
| SEQ ID NO: 18 | | CDR-L3 | FQGSHVPVT |
| SEQ ID NO: 19 | ABC_HG1N07 | CDR-H1 | GFTFRNY |
| SEQ ID NO: 20 | | CDR-H2 | SESGNY |
| SEQ ID NO: 21 | | CDR-H3 | DDWEGRAMDY |
| SEQ ID NO: 22 | | CDR-L1 | RASRDIGSSLN |
| SEQ ID NO: 23 | | CDR-L2 | ATSSLDS |
| SEQ ID NO: 24 | | CDR-L3 | LQYASSPWT |

Amino acid sequences of $V_H$ and $V_L$ domains of mouse anti-KLRG1 antibodies are set forth in the Sequence Listing and are enumerated as listed in Table 3

TABLE 3

Variable region amino acid sequences for mouse anti-KLRG1 antibodies

| SEQ ID NO. | mAb | $V_H$/$V_L$ | Amino Acid Sequence |
|---|---|---|---|
| SEQ ID NO: 25 | ABC_G1N01 | $V_H$ | QVILKESGPGILQPSQTLSLTCSFSGFSLTTFGMGIGWIRHPSGKALEWLAHIWWNDDKSYNSALKSRLTISKDTSKNQVFLRLANVATADTATYYCARTIYYGNYLTFYAMEHWGQGTSVTVSS |
| SEQ ID NO: 26 | | $V_L$ | DVLLTQTPLSLPVSLGDQASISCRSSQNIVHSNGNTYLEWYLLKPGQSPKLLIFKVSNRFSGVPDKFSGSGSGTDFTLKIRRVEAEDLGIYYCFQGSHVPPTFGAGTKLELK |
| SEQ ID NO: 27 | ABC_G1N02 | $V_H$ | QVTLKESGPGILQPSQTLSLTCSVSGFSLSTFGMGVGWIRQPSGKGLEWLAHIWWDDDKWYELALKSRLTISKDSSKNQVFLKIANVDTADTATYFCARVIYYGSRSAYYSMDYWGPGTSVTVSS |
| SEQ ID NO: 28 | | $V_L$ | DVLMTQTPLSLPVSLGAQASISCKSSQSIVHSNGHTYLEWYLQKPGQSPKILIYKVSNRFSGVPDRFSGSGSGTDFTLKISRVEAEDLGVYYCFQGSHVPVTFGAGTKLELK |
| SEQ ID NO: 29 | ABC_G1N03 | $V_H$ | QVHLQQSGPELVKPGASVKLSCKASGDTFTTYDITWVKQRPGQGLEWIGWIYPKDGRTQNSEKFKDKATLTVDTSSTTAYMELHSLTSEDSAVYFCARRGQFGPYFDHWGQGSTLTVSS |
| SEQ ID NO: 30 | | $V_L$ | VIQMTQSSSFLSASLGGRVSITCRASDHIYNWLAWYQQKPGNAPRLLISGATSLETGIPSRFSGGGSGKDYTLTIISLQTEDIASYYCQQYWNTPPTFGGGTKVEIK |
| SEQ ID NO: 31 | ABC_G1N04 | $V_H$ | DVQLVESGGGLVQPGGSRKLSCAASGFSFSTFGMHWVRQVPEKGLEWVAYISSGSYSIFYADSVKGRFTISRDNPKNTLFLQMTSLRSEDTAIYYCTRTRDSGSSPHYFDYWGQGTTVTVSS |
| SEQ ID NO: 32 | | $V_L$ | DIVLTQSPTSLAVSLGQRATISCRASKSVDSYGISFMNWFQQKPGQSPKLLIYGASNRGSGVPARFSGSGSGTDFSLNIHPMEEDDTAMYFCQQSKEGPFTFGTGTKLELR |
| SEQ ID NO: 33 | ABC_G1N05 | $V_H$ | EVLLMESGGDLVKPGGSLKLSCAASGFTFSSYDMSWVRQTPDKRLEWVATISSSGRYTFYPDNVKGRFTISRDNAKNTLYLQVSNLKSEDTAMYYCSRTGVTTVVFTDYFDYWGQGTLTVSS |

TABLE 3-continued

Variable region amino acid sequences for mouse anti-KLRG1 antibodies

| SEQ ID NO. | mAb | $V_H/V_L$ | Amino Acid Sequence |
|---|---|---|---|
| SEQ ID NO: 34 | | $V_L$ | DIQMTQSPSSLSASLGERVSLTCRASQDIGNSLNWLQQGPDGTIKRLIYATSSLDSGVPKRFSGSRSGSTYSLTISSLESEDFVAYYCLQYLSSPPTFGGGTKLEIK |
| SEQ ID NO: 35 | ABC_G1N06 | $V_H$ | QVQLKQSGPGLVQPSQSLSITCTVSGFSLTTHAVHWVRQSPGKGLDWLGVIWSGGNTDYNAAFISRLTISKDNSKSQVFFKMNSLQADDTAIYYCVRLLLPAMDYWGQGTSVTVSS |
| SEQ ID NO: 36 | | $V_L$ | QIVLTQSPAIIVISASLGERVTMTCTATSSVSSTYLHWYRQKPGSSPKLWIYSTSTLASGVPVRFRGSGSGTSYSLTISSMEAEDAATYYCHQYRRSPYTFGGGTKLEIK |
| SEQ ID NO: 37 | ABC_G1N07 | $V_H$ | EVQLVESGGGLVKPGGSLKLSCTASGFTFRNYAMSWVRQTPEKRLEWVATISESGNYNNYPDNVKGRLTISRDNAKNNLYLQMSLLKSEDTAMYYCVRDDWEGRAMDYWGQGTSVTVSS |
| SEQ ID NO: 38 | | $V_L$ | GIQMTQSPSSLSASLGERVSLTCRASRDIGSSLNWLQQKPDGTIKRLIYATSSLDSGVPKRFSGSRSGTDYSLTISSLESEDFVDYFCLQYASSPWTFGGGTKLEIK |
| SEQ ID NO: 39 | ABC_G1N08 | $V_H$ | QVQLQQSGAELAKPGASVKLSCKASGYTFTSYFLHWVKQRPGQGLEWIGYMNPSSGYTKCNQKFKDKATLTADKSSSTAYMQVSSLTYEDSAVYYCARDRIGYWDFDVWGTGTTVTVSS |
| SEQ ID NO: 40 | | $V_L$ | DVVMTQSQKFMSTTVGDRVSITCKASQNVGTAVAWYQQKPGQSPKLLIYSASNRYTGVPDRFTGSGSGTDFTLTITNMQSEDLADYFCQQYSSYLTFGAGTKLDLK |

Particular nonlimiting illustrative embodiments of the antibodies are referred to as ABC_G1N01, ABC_G1N02, ABC_G1N03, ABC_G1N04, ABC_G1N05, ABC_G1N06, ABC_G1N07, and ABC_G1N08. Amino acid sequences of CDRs within the $V_H$ and $V_L$ domains of the illustrative embodiments are set forth in the Sequence Listing and are enumerated as listed in Table 4.

TABLE 4

CDR amino acid sequences for mouse anti-KLRG1 antibodies

| SEQ ID NO. | mAb | CDR | Sequence |
|---|---|---|---|
| SEQ ID NO: 41 | ABC_G1N01 | CDR-H1 | GFSLTTFGM |
| SEQ ID NO: 42 | | CDR-H2 | WWNDD |
| SEQ ID NO: 43 | | CDR-H3 | TIYYGNYLTFYAMEH |
| SEQ ID NO: 44 | | CDR-L1 | RSSQNIVHSNGNTYLE |
| SEQ ID NO: 45 | | CDR-L2 | KVSNRFS |
| SEQ ID NO: 46 | | CDR-L3 | FQGSHVPPT |
| SEQ ID NO: 47 | ABC_G1N02 | CDR-H1 | GFSLSTFGM |
| SEQ ID NO: 48 | | CDR-H2 | WWDDD |
| SEQ ID NO: 49 | | CDR-H3 | VIYYGSRSAYYSMDY |
| SEQ ID NO: 50 | | CDR-L1 | KSSQSIVHSNGHTYLE |
| SEQ ID NO: 51 | | CDR-L2 | KVSNRFS |
| SEQ ID NO: 52 | | CDR-L3 | FQGSHVPVT |
| SEQ ID NO: 53 | ABC_G1N03 | CDR-H1 | GDTFTTYDIT |
| SEQ ID NO: 54 | | CDR-H2 | YPKDGR |
| SEQ ID NO: 55 | | CDR-H3 | RGQFGPYFDH |
| SEQ ID NO: 56 | | CDR-L1 | RASDHIYNWLA |
| SEQ ID NO: 57 | | CDR-L2 | GATSLET |
| SEQ ID NO: 58 | | CDR-L3 | RGQFGPYFDH |
| SEQ ID NO: 59 | ABC_G1N04 | CDR-H1 | GFSFSTF |
| SEQ ID NO: 60 | | CDR-H2 | SSGSYS |
| SEQ ID NO: 61 | | CDR-H3 | TRTRDSGSSPHYFDY |
| SEQ ID NO: 62 | | CDR-L1 | RASKSVDSYGISFMN |
| SEQ ID NO: 63 | | CDR-L2 | GASNRGS |
| SEQ ID NO: 64 | | CDR-L3 | QQSKEGPFT |
| SEQ ID NO: 65 | ABC_G1N05 | CDR-H1 | GFTFSSY |
| SEQ ID NO: 66 | | CDR-H2 | SSSGRY |
| SEQ ID NO: 67 | | CDR-H3 | TGVTTVVFTDYFDY |
| SEQ ID NO: 68 | | CDR-L1 | SQDIGNS |
| SEQ ID NO: 69 | | CDR-L2 | SSLDS |

TABLE 4-continued

CDR amino acid sequences for mouse anti-KLRG1 antibodies

| SEQ ID NO. | mAb | CDR | Sequence |
|---|---|---|---|
| SEQ ID NO: 70 | | CDR-L3 | LQYLSSPPTF |
| SEQ ID NO: 71 | ABC_G1N06 | CDR-H1 | GFSLTTH |
| SEQ ID NO: 72 | | CDR-H2 | WSGGN |
| SEQ ID NO: 73 | | CDR-H3 | LLLPAMDY |
| SEQ ID NO: 74 | | CDR-L1 | TATSSVSSTYLH |
| SEQ ID NO: 75 | | CDR-L2 | STSTLAS |
| SEQ ID NO: 76 | | CDR-L3 | HQYRRSPYT |
| SEQ ID NO: 77 | ABC_G1N07 | CDR-H1 | GFTFRNY |
| SEQ ID NO: 78 | | CDR-H2 | SESGNY |
| SEQ ID NO: 79 | | CDR-H3 | DDWEGRAMDY |
| SEQ ID NO: 80 | | CDR-L1 | RASRDIGSSLN |
| SEQ ID NO: 81 | | CDR-L2 | ATSSLDS |
| SEQ ID NO: 82 | | CDR-L3 | LQYASSPWT |
| SEQ ID NO: 83 | ABC_G1N08 | CDR-H1 | GYTFTSY |
| SEQ ID NO: 84 | | CDR-H2 | NPSSGY |
| SEQ ID NO: 85 | | CDR-H3 | DRIGYWDFDV |
| SEQ ID NO: 86 | | CDR-L1 | KASQNVGTAVA |
| SEQ ID NO: 87 | | CDR-L2 | SASNRYT |
| SEQ ID NO: 88 | | CDR-L3 | QQYSSYLT |

Anti-KLRG1 antibodies may optionally comprise antibody constant regions or parts thereof. For example, a $V_L$ domain may have attached, at its C terminus, antibody light chain constant domains including human Cκ or Cλ chains. Similarly, a specific antigen-binding domain based on a $V_H$ domain may have attached all or part of an immunoglobulin heavy chain derived from any antibody isotype, e.g., IgG, IgA, IgE, and IgM and any of the isotype sub-classes, which include but are not limited to, IgG1 and IgG4. In the exemplary embodiments, ABC_HG1N01, ABC_HG1N02, ABC_HG1N07, ABC_G1N01, ABC_G1N02, ABC_G1N03, ABC_G1N04, ABC_G1N05, ABC_G1N06, ABC_G1N07, and ABC_G1N08 antibodies comprise C-terminal fragments of heavy and light chains of human IgG1λ or IgG1κ. The DNA and amino acid sequences for the C-terminal fragment of are well known in the art (see, e.g., Kabat et al., Sequences of Proteins of Immunological Interest, No. 91-3242, National Institutes of Health Publications, Bethesda, Md., 1991).

Certain embodiments comprise a $V_H$ and/or $V_L$ domain of an Fv fragment from ABC_HG1N01, ABC_HG1N02, ABC_HG1N07, ABC_G1N01, ABC_G1N02, ABC_G1N03, ABC_G1N04, ABC_G1N05, ABC_G1N06, ABC_G1N07, and ABC_G1N08. Further embodiments comprise at least one CDR of any of these $V_H$ and $V_L$ domains. Antibodies, comprising at least one of the CDR sequences set out in SEQ ID NO:1, SEQ ID NO:2, SEQ ID NO:3, SEQ ID NO:4, SEQ ID NO:5, SEQ ID NO:6, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, and SEQ ID NO:38 are encompassed within the scope of this invention. An embodiment, for example, comprises an H3 fragment of the $V_H$ domain of antibodies chosen from at least one of ABC_HG1N01, ABC_HG1N02, ABC_HG1N07ABC_G1N01, ABC_G1N02, ABC_G1N03, ABC_G1N04, ABC_G1N05, ABC_G1N06, ABC_G1N07, and ABC_G1N08.

In certain embodiments, the $V_H$ and/or $V_L$ domains may be germlined, i.e., the framework regions (FRs) of these domains are mutated using conventional molecular biology techniques to match those produced by the germline cells. In other embodiments, the framework sequences remain diverged from the consensus germline sequences.

In certain embodiments, the antibodies specifically bind an epitope within the ECD of human or mouse KLRG1, with an affinity, as expressed in $K_D$, of at least about 2 nM, 1 nm, 100 pM, 10 pM, or 5 pM. The amino acid sequences of ECDs of human and cynomolgus KLRG1 are set out in SEQ ID NO:89 and SEQ ID NO:90, as listed in Table 6.

It is contemplated that antibodies of the invention may also bind with other proteins, including, for example, recombinant proteins comprising all or a portion of KLRG1.

One of ordinary skill in the art will recognize that the antibodies of this invention may be used to detect, measure, and inhibit proteins that differ somewhat from KLRG1. The antibodies are expected to retain the specificity of binding so long as the target protein comprises a sequence which is at least about 60%, 70%, 80%, 90%, 95%, or more identical to any sequence of at least 130, 100, 80, 60, 40, or 20 of contiguous amino acids in the sequence set forth SEQ ID NO:89 or SEQ ID NO:90. The percent identity is determined by standard alignment algorithms such as, for example, Basic Local Alignment Tool (BLAST) described in Altshul et al. (1990) J. Mol. Biol., 215: 403-410, the algorithm of Needleman et al. (1970) J. Mol. Biol., 48: 444-453, or the algorithm of Meyers et al. (1988) Comput. Appl. Biosci., 4: 11-17.

In addition to the sequence homology analyses, epitope mapping (see, e.g., Epitope Mapping Protocols, ed. Morris, Humana Press, 1996) and secondary and tertiary structure analyses can be carried out to identify specific 3D structures assumed by the disclosed antibodies and their complexes with antigens. Such methods include, but are not limited to, X-ray crystallography (Engstom (1974) Biochem. Exp. Biol., 11:7-13) and computer modeling of virtual representations of the presently disclosed antibodies (Fletterick et al. (1986) Computer Graphics and Molecular Modeling, in Current Communications in Molecular Biology, Cold Spring Harbor Laboratory, Cold Spring Harbor, N.Y.).

Derivatives

This disclosure also provides a method for obtaining an antibody specific for KLRG1. CDRs in such antibodies are not limited to the specific sequences of $V_H$ and $V_L$ identified in Tables 1 and 3, and may include variants of these sequences that retain the ability to specifically bind KLRG1. Such variants may be derived from the sequences listed in Tables 1 and 3 by a skilled artisan using techniques well known in the art. For example, amino acid substitutions, deletions, or additions, can be made in the FRs and/or in the CDRs. While changes in the FRs are usually designed to improve stability and immunogenicity of the antibody, changes in the CDRs are typically designed to increase affinity of the antibody for its target. Variants of FRs also include naturally occurring immunoglobulin allotypes. Such affinity-increasing changes may be determined empirically by routine techniques that involve altering the CDR and testing the affinity antibody for its target. For example, conservative amino acid substitutions can be made within any one of the disclosed CDRs. Various alterations can be made according to the methods described in Antibody Engineering, 2nd ed., Oxford University Press, ed. Borrebaeck, 1995. These include but are not limited to nucleotide sequences that are altered by the substitution of different codons that encode a functionally equivalent amino acid residue within the sequence, thus producing a "silent" change. For example, the nonpolar amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Substitutes for an amino acid within the sequence may be selected from other members of the class to which the amino acid belongs (see Table 5). Furthermore, any native residue in the polypeptide may also be substituted with alanine (see, e.g., MacLennan et al. (1998) Acta Physiol. Scand. Suppl. 643:55-67; Sasaki et al. (1998) Adv. Biophys. 35:1-24).

TABLE 5

Exemplary conservative substitutions:

| Residue | Conservative substitution |
|---|---|
| Ala (A) | Ser (S) |
| Arg (R) | Lys (K) |
| Asn (N) | Gln (Q); His (H) |
| Asp (D) | Glu (E) |
| Cys (C) | Ser (S) |
| Gln (Q) | Asn (N) |
| Glu (E) | Asp (D) |
| Gly (G) | Pro (P) |
| His (H) | Asn (N), Gln (Q) |
| Ile (I) | Leu (L), Val (V) |
| Leu (L) | Ile (I), Val (V) |
| Lys (K) | Arg (R), Gln (Q) |
| Met (M) | Leu (L), Ile (I) |
| Phe (F) | Met (M), Leu (L), Tyr (Y) |
| Ser (S) | Thr (T); Gly (G) |
| Thr (T) | Ser (S), Val (V) |
| Trp (W) | Tyr (Y) |
| Tyr (Y) | Trp (W), Phe (F) |
| Val (V) | Ile (I), Leu (L) |
| Pro (P) | — |

Derivatives and analogs of antibodies of the invention can be produced by various techniques well known in the art, including recombinant and synthetic methods (Maniatis (1990) Molecular Cloning, A Laboratory Manual, 2nd ed., Cold Spring Harbor Laboratory, Cold Spring Harbor, N.Y., and Bodansky et al. (1995) The Practice of Peptide Synthesis, 2nd ed., Spring Verlag, Berlin, Germany).

In one embodiment, a method for making a $V_H$ domain which is an amino acid sequence variant of a $V_H$ domain of the invention comprises a step of adding, deleting, substituting, or inserting one or more amino acids in the amino acid sequence of the presently disclosed $V_H$ domain, optionally combining the $V_H$ domain thus provided with one or more $V_L$ domains, and testing the $V_H$ domain or $V_H/V_L$ combination or combinations for a specific binding to KLRG1 and, optionally, testing the ability of such antigen-binding domain to modulate KLRG1 activity. The $V_L$ domain may have an amino acid sequence that is identical or is substantially as set out according to Tables 1 and 3.

An analogous method can be employed in which one or more sequence variants of a $V_L$ domain disclosed herein are combined with one or more $V_H$ domains.

A further aspect of the disclosure provides a method of preparing antigen-binding fragment that specifically binds with KLRG1. The method comprises:

(a) providing a starting repertoire of nucleic acids encoding a $V_H$ domain that either includes a CDR3 to be replaced or lacks a CDR3 encoding region;

(b) combining the repertoire with a donor nucleic acid encoding an amino acid sequence substantially as set out herein for a $V_H$ CDR3 (i.e., H3) such that the donor nucleic acid is inserted into the CDR3 region in the repertoire, so as to provide a product repertoire of nucleic acids encoding a $V_H$ domain;

(c) expressing the nucleic acids of the product repertoire;

(d) selecting a binding fragment specific for KLRG1; and (e) recovering the specific binding fragment or nucleic acid encoding it.

Again, an analogous method may be employed in which a $V_L$ CDR3 (i.e., L3) of the invention is combined with a repertoire of nucleic acids encoding a $V_L$ domain, which either include a CDR3 to be replaced or lack a CDR3 encoding region. The donor nucleic acid may be selected from nucleic acids encoding an amino acid sequence substantially as set out in SEQ ID NOs:7-24 and 41-88.

A sequence encoding a CDR of the invention (e.g., CDR3) may be introduced into a repertoire of variable domains lacking the respective CDR (e.g., CDR3), using recombinant DNA technology, for example, using methodology described by Marks et al. (Bio/Technology (1992) 10: 779-783). In particular, consensus primers directed at or adjacent to the 5' end of the variable domain area can be used in conjunction with consensus primers to the third framework region of human $V_H$ genes to provide a repertoire of $V_H$ variable domains lacking a CDR3. The repertoire may be combined with a CDR3 of a particular antibody. Using analogous techniques, the CDR3-derived sequences may be shuffled with repertoires of $V_H$ or $V_L$ domains lacking a CDR3, and the shuffled complete $V_H$ or $V_L$ domains combined with a cognate $V_L$ or $V_H$ domain to make the KLRG1-specific antibodies of the invention. The repertoire may then be displayed in a suitable host system such as the phage display system such as described in WO92/01047 so that suitable antigen-binding fragments can be selected.

Analogous shuffling or combinatorial techniques are also disclosed by Stemmer (Nature (1994) 370: 389-391), who describes the technique in relation to a 0-lactamase gene but observes that the approach may be used for the generation of antibodies.

In further embodiments, one may generate novel $V_H$ or $V_L$ regions carrying one or more sequences derived from the sequences disclosed herein using random mutagenesis of one or more selected $V_H$ and/or $V_L$ genes. One such technique, error-prone PCR, is described by Gram et al. (Proc. Nat. Acad. Sci. U.S.A. (1992) 89: 3576-3580).

Another method that may be used is to direct mutagenesis to CDRs of $V_H$ or $V_L$ genes. Such techniques are disclosed by Barbas et al. (Proc. Nat. Acad. Sci. U.S.A. (1994) 91: 3809-3813) and Schier et al. (J. Mol. Biol. (1996) 263: 551-567).

Similarly, one or more, or all three CDRs may be grafted into a repertoire of $V_H$ or $V_L$ domains, which are then screened for an antigen-binding fragment specific for KLRG1.

A portion of an immunoglobulin variable domain will comprise at least one of the CDRs substantially as set out herein and, optionally, intervening framework regions from the scFv fragments as set out herein. The portion may include at least about 50% of either or both of FR1 and FR4, the 50% being the C-terminal 50% of FR1 and the N-terminal 50% of FR4. Additional residues at the N-terminal or C-terminal end of the substantial part of the variable domain may be those not normally associated with naturally occurring variable domain regions. For example, construction of antibodies by recombinant DNA techniques may result in the introduction of N- or C-terminal residues encoded by linkers introduced to facilitate cloning or other manipulation steps. Other manipulation steps include the introduction of linkers to join variable domains to further protein sequences including immunoglobulin heavy chain constant regions, other variable domains (for example, in the production of diabodies), or proteinaceous labels as discussed in further detail below.

Although the embodiments illustrated in the Examples comprise a "matching" pair of $V_H$ and $V_L$ domains, a skilled artisan will recognize that alternative embodiments may comprise antigen-binding fragments containing only a single CDR from either $V_L$ or $V_H$ domain. Either one of the single chain specific binding domains can be used to screen for complementary domains capable of forming a two-domain specific antigen-binding fragment capable of, for example, binding to KLRG1. The screening may be accomplished by phage display screening methods using the so-called hierarchical dual combinatorial approach disclosed in WO92/01047, in which an individual colony containing either an H or L chain clone is used to infect a complete library of clones encoding the other chain (L or H) and the resulting two-chain specific binding domain is selected in accordance with phage display techniques as described.

Anti-KLRG1 antibodies described herein can be linked to another functional molecule, e.g., another peptide or protein (albumin, another antibody, etc.), toxin, radioisotope, cytotoxic or cytostatic agents. For example, the antibodies can be linked by chemical cross-linking or by recombinant methods. The antibodies may also be linked to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192; or 4,179,337. The antibodies can be chemically modified by covalent conjugation to a polymer, for example, to increase their circulating half-life. Exemplary polymers and methods to attach them are also shown in U.S. Pat. Nos. 4,766,106; 4,179,337; 4,495,285, and 4,609,546.

The disclosed antibodies may also be altered to have a glycosylation pattern that differs from the native pattern. For example, one or more carbohydrate moieties can be deleted and/or one or more glycosylation sites added to the original antibody. Addition of glycosylation sites to the presently disclosed antibodies may be accomplished by altering the amino acid sequence to contain glycosylation site consensus sequences known in the art. Another means of increasing the number of carbohydrate moieties on the antibodies is by chemical or enzymatic coupling of glycosides to the amino acid residues of the antibody. Such methods are described in WO 87/05330 and in Aplin et al. (1981) CRC Crit. Rev. Biochem., 22: 259-306. Removal of any carbohydrate moieties from the antibodies may be accomplished chemically or enzymatically, for example, as described by Hakimuddin et al. (1987) Arch. Biochem. Biophys., 259: 52; and Edge et al. (1981) Anal. Biochem., 118: 131 and by Thotakura et al. (1987) Meth. Enzymol., 138: 350. The antibodies may also be tagged with a detectable, or functional, label. Detectable labels include radiolabels such as $^{131}I$ or $^{99}Tc$, which may also be attached to antibodies using conventional chemistry. Detectable labels also include enzyme labels such as horseradish peroxidase or alkaline phosphatase. Detectable labels further include chemical moieties such as biotin, which may be detected via binding to a specific cognate detectable moiety, e.g., labeled avidin.

Antibodies, in which CDR sequences differ only insubstantially from those set out in SEQ ID NO:1, SEQ ID NO:2, SEQ ID NO:3, SEQ ID NO:4, SEQ ID NO: 5, SEQ ID NO:6, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, or SEQ ID NO:40 are encompassed within the scope of this invention. Typically, an amino acid is substituted by a related amino acid having similar charge, hydrophobic, or stereochemical characteristics. Such substitutions would be within the ordinary skills of an artisan. Unlike in CDRs, more substantial changes can be made in FRs without adversely affecting the binding properties of an antibody. Changes to FRs include, but are not limited to, humanizing a non-human derived or engineering certain framework residues that are important for antigen contact or for stabilizing the binding site, e.g., changing the class or subclass of the constant region, changing specific amino acid residues which might alter the effector function such as Fc receptor binding, e.g., as described in U.S. Pat. Nos. 5,624,821 and 5,648,260 and Lund et al. (1991) J. Immun. 147: 2657-2662 and Morgan et al. (1995) Immunology 86: 319-324, or changing the species from which the constant region is derived.

One of skill in the art will appreciate that the modifications described above are not all-exhaustive, and that many other modifications would obvious to a skilled artisan in light of the teachings of the present disclosure.

Nucleic Acids, Cloning and Expression Systems

The present disclosure further provides isolated nucleic acids encoding the disclosed antibodies. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

The nucleic acids provided herein comprise a coding sequence for a CDR, a $V_H$ domain, and/or a $V_L$ domain disclosed herein.

The present disclosure also provides constructs in the form of plasmids, vectors, phagemids, transcription or expression cassettes which comprise at least one nucleic acid encoding a CDR, a $V_H$ domain, and/or a $V_L$ domain disclosed here.

The disclosure further provides a host cell which comprises one or more constructs as above.

Also provided are nucleic acids encoding any CDR (H1, H2, H3, L1, L2, or L3), $V_H$ or $V_L$ domain, as well as methods of making of the encoded products. The method comprises expressing the encoded product from the encoding nucleic acid. Expression may be achieved by culturing under appropriate conditions recombinant host cells containing the nucleic acid. Following production by expression a $V_H$ or $V_L$ domain, or specific binding member may be isolated and/or purified using any suitable technique, then used as appropriate.

Antigen-binding fragments, $V_H$ and/or $V_L$ domains, and encoding nucleic acid molecules and vectors may be isolated and/or purified from their natural environment, in substantially pure or homogeneous form, or, in the case of nucleic acid, free or substantially free of nucleic acid or genes of origin other than the sequence encoding a polypeptide with the required function.

Systems for cloning and expression of a polypeptide in a variety of different host cells are well known in the art. For cells suitable for producing antibodies, see Gene Expression Systems, Academic Press, eds. Fernandez et al., 1999. Briefly, suitable host cells include bacteria, plant cells, mammalian cells, and yeast and baculovirus systems. Mammalian cell lines available in the art for expression of a heterologous polypeptide include Chinese hamster ovary cells, HeLa cells, baby hamster kidney cells, NS0 mouse myeloma cells, and many others. A common bacterial host is E. coli. Any protein expression system compatible with the invention may be used to produce the disclosed antibodies. Suitable expression systems include transgenic animals described in Gene Expression Systems, Academic Press, eds. Fernandez et al., 1999.

Suitable vectors can be chosen or constructed, so that they contain appropriate regulatory sequences, including promoter sequences, terminator sequences, polyadenylation sequences, enhancer sequences, marker genes and other sequences as appropriate. Vectors may be plasmids or viral, e.g., phage, or phagemid, as appropriate. For further details see, for example, Sambrook et al., Molecular Cloning: A Laboratory Manual, 2nd ed., Cold Spring Harbor Laboratory Press, 1989. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, 2nd Edition, eds. Ausubel et al., John Wiley & Sons, 1992.

A further aspect of the disclosure provides a host cell comprising a nucleic acid as disclosed here. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction of the nucleic acid into the cells may be followed by causing or allowing expression from the nucleic acid, e.g., by culturing host cells under conditions for expression of the gene.

METHODS OF USE

The disclosed anti-KLRG1 antibodies are capable of modulating the KLRG1-associated modulation of the immune responses. In particular embodiments, the activation of cytotoxic T and NK cells is mediated by modulation of KLRG1 signaling. The disclosed antibodies can act as either agonists or antagonists of KLRG1, depending on the method of their use. The antibodies can be used to prevent, diagnose, or treat medical disorders in mammals, especially, in humans. Antibodies of the invention can also be used for isolating KLRG1 or KLRG1-expressing cells. Furthermore, the antibodies can be used to treat a subject at risk of or susceptible to a disorder or having a disorder associated with aberrant KLRG1 expression or function.

Antibodies of the invention can be used in circumstances where modulation of cytotoxic T and NK cell activation may be desirable, for example, in certain types of cancers and infectious diseases.

When diminished lymphocyte activation is desirable, the anti-KLRG1 antibodies of the invention may be used as agonists to KLRG1 in order to enhance the KLRG1-associated attenuation of cytotoxic (or CD8+) T and NK cell activation.

Under certain circumstances, it may be desirable to elicit or enhance a patient's immune response in order to treat cancer or an infectious disease. The disorders being treated or prevented by the disclosed methods include but are not limited to infections with microbes (e.g. bacteria), viruses (e.g., systemic viral infections such as influenza, viral skin diseases such as herpes or shingles), or parasites; and cancer (e.g., melanoma and prostate cancers).

Cytotoxic T and NK cell activation with anti-KLRG1 antibodies enhances T and NK cell responses. In such cases, antibodies act as antagonists of KLRG1. Thus, in some embodiments, the antibodies can be used to inhibit or reduce the downregulatory activity associated with KLRG1, i.e., the activity associated with downregulation of cytotoxic T and NK cell activation. As demonstrated in the Examples, a blockade of KLRG1/E-cadherin interaction with antagonizing anti-KLRG1 antibodies leads to enhanced T cell proliferative responses and IFNγ secretion by these cells, consistent with a downregulatory role for the KLRG1 pathway in cytotoxic T and NK cell activation. In various embodiments, the antibodies inhibit binding of E-cadherin to KLRG1 with an IC50 of less than about 50 nM, and more preferably less than about 40, 30, 20, 10, or 5 nM. Inhibition of E-cadherin binding can be measured as described in Example 6 or using techniques known in the art.

The antibodies or antibody compositions of the present invention are administered in therapeutically effective amounts. Generally, a therapeutically effective amount may vary with the subject's age, condition, and sex, as well as the severity of the medical condition of the subject. A therapeutically effective amount of antibody ranges from about 0.001 to about 30 mg/kg body weight, preferably from about 0.01 to about 25 mg/kg body weight, from about 0.1 to about 20 mg/kg body weight, or from about 1 to about 10 mg/kg. The dosage may be adjusted, as necessary, to suit observed effects of the treatment. The appropriate dose is chosen based on clinical indications by a treating physician.

The antibodies may be given as a bolus dose, to maximize the circulating levels of antibodies for the greatest length of time after the dose. Continuous infusion may also be used after the bolus dose.

Immune cells (e.g., T cells or NK cells) can also be isolated from a patient and incubated ex vivo with antibodies of the invention. In some embodiments, T cell and NK cell activation can be modulated by removing immune cells from a subject, contacting the immune cells in vitro with an anti-KLRG1 antibody of the invention). In such embodiments, the anti-KLRG1 antibody may be used in a multivalent form such that KLRG1 molecules on the surface of an immune cell become "crosslinked" upon binding to such antibodies. For example, the anti-KLRG1 antibodies can be bound to solid support, such as beads, or crosslinked via a secondary antibody. The immune cells may be then isolated using methods known in the art and reimplanted into the patient.

In another aspect, the antibodies of the invention can be used as a targeting agent for delivery of another therapeutic or a cytotoxic agent (e.g., a toxin) to a cell expressing KLRG1. The method includes administering an anti-KLRG1 antibody coupled to a therapeutic or a cytotoxic agent or under conditions that allow binding of the antibody to KLRG1.

The antibodies of the invention may also be used to detect the presence of KLRG1 in biological samples. The amount of KLRG1 detected may be correlated with the expression level of KLRG1, which, in turn, is correlated with the activation status of immune cells (e.g., activated T cells or NK cells) in the subject.

Detection methods that employ antibodies are well known in the art and include, for example, ELISA, radioimmunoassay, immunoblot, Western blot, immunofluorescence, immunoprecipitation. The antibodies may be provided in a diagnostic kit that incorporates one or more of these techniques to detect KLRG1. Such a kit may contain other components, packaging, instructions, or other material to aid the detection of the protein.

Where the antibodies are intended for diagnostic purposes, it may be desirable to modify them, for example, with a ligand group (such as biotin) or a detectable marker group (such as a fluorescent group, a radioisotope or an enzyme). If desired, the antibodies of the invention may be labeled using conventional techniques. Suitable detectable labels include, for example, fluorophores, chromophores, radioactive atoms, electron-dense reagents, enzymes, and ligands having specific binding partners. Enzymes are typically detected by their activity. For example, horseradish peroxidase can be detected by its ability to convert tetramethylbenzidine (TMB) to a blue pigment, quantifiable with a spectrophotometer. For detection, suitable binding partners include, but are not limited to, biotin and avidin or streptavidin, IgG and protein A, and the numerous receptor-ligand couples known in the art. Other permutations and possibilities will be readily apparent to those of ordinary skill in the art, and are considered as equivalents within the scope of the instant invention.

Antibodies of the invention can be used in screening methods to identify inhibitors of the KLRG1 pathway effective as therapeutics. In such a screening assay, a first binding mixture is formed by combining KLRG1 and an antibody of the invention; and the amount of binding in the first binding mixture (M0) is measured. A second binding mixture is also formed by combining KLRG1, the antibody, and the compound or agent to be screened, and the amount of binding in the second binding mixture (M1) is measured. A compound to be tested may be another anti-KLRG1 antibody, as illustrated in the Examples. The amounts of binding in the first and second binding mixtures are then compared, for example, by calculating the M1/M0 ratio. The compound or agent is considered to be capable of modulating a KLRG1-associated downregulation of immune responses if a decrease in binding in the second binding mixture as compared to the first binding mixture is observed. The formulation and optimization of binding mixtures is within the level of skill in the art, such binding mixtures may also contain buffers and salts necessary to enhance or to optimize binding, and additional control assays may be included in the screening assay of the invention. Compounds found to reduce the KLRG1-antibody binding by at least about 10% (i.e., M1/M0<0.9), preferably greater than about 30% may thus be identified and then, if desired, secondarily screened for the capacity to ameliorate a disorder in other assays or animal models as described below. The strength of the binding between KLRG1 and an antibody can be measured using, for example, an enzyme-linked immunoadsorption assay (ELISA), radio-immunoassay (RIA), surface plasmon resonance-based technology (e.g., Biacore), all of which are techniques well known in the art.

The compound may then be tested in vitro as described in the Examples or in an animal model. Preliminary doses as, for example, determined according to animal tests, and the scaling of dosages for human administration is performed according to art-accepted practices. Toxicity and therapeutic efficacy can be determined by standard pharmaceutical procedures in cell cultures or experimental animals. The data obtained from the cell culture assays or animal studies can be used in formulating a range of dosage for use in humans. Therapeutically effective dosages achieved in one animal model can be converted for use in another animal, including humans, using conversion factors known in the art (see, e.g., Freireich et al. (1966) Cancer Chemother. Reports, 50(4): 219-244).

Pharmaceutical Compositions and Methods of Administration

The disclosure provides compositions comprising anti-KLRG1 antibodies. Such compositions may be suitable for pharmaceutical use and administration to patients. The compositions typically comprise one or more antibodies of the present invention and a pharmaceutically acceptable excipient. The phrase "pharmaceutically acceptable excipient" includes any and all solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. The administration may, for example, be intravenous, intraperitoneal, intramuscular, intracavity, subcutaneous or transdermal. It may also be possible to obtain compositions which may be topically or orally administered, or which may be capable of transmission across mucous membranes.

Solutions or suspensions used for intradermal or subcutaneous application typically include one or more of the following components: a sterile diluent such as water for injection, saline solution, fixed oils, polyethylene glycols, glycerin, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic. Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars; polyalcohols such as mannitol, sorbitol, and sodium chloride in the composition. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and/or by the use of surfactants. Prolonged absorption of the injectable compositions can be brought about by including in the composition an agent which delays absorption, for example, aluminum monostearate, and gelatin.

Oral compositions generally include an inert diluent or an edible carrier. They can be enclosed in gelatin capsules or compressed into tablets. For oral administration, the antibodies can be combined with excipients and used in the form of tablets, troches, or capsules. Pharmaceutically compatible binding agents, and/or adjuvant materials can be included as part of the composition. The tablets, pills, capsules, troches, and the like can contain any of the following ingredients, or compounds of a similar nature; a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, detergents, bile salts, and fusidic acid derivatives. Transmucosal administration may be accomplished, for example, through the use of lozenges, nasal sprays, inhalers, or suppositories; For example, in case of antibodies that comprise the Fc portion, compositions may be capable of transmission across mucous membranes in intestine, mouth, or lungs (e.g., via the FcRn receptor-mediated pathway as described in U.S. Pat. No. 6,030,613). For transdermal administration, the active compounds may be formulated into ointments, salves, gels, or creams as generally known in the art. For administration by inhalation, the antibodies may be delivered in the form of an aerosol spray from pressured container or dispenser, which contains a suitable propellant, e.g., a gas such as carbon dioxide, or a nebulizer.

In certain embodiments, the presently disclosed antibodies are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions containing the presently disclosed antibodies can also be used as pharmaceutically acceptable carriers. These can be prepared according to methods known to those skilled in the art, for example, as described in U.S. Pat. No. 4,522,811.

It may be advantageous to formulate oral or parenteral compositions in a dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of the composition of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred.

For any composition used in the present invention, the therapeutically effective dose can be estimated initially from cell culture assays. Examples of suitable bioassays include DNA replication assays, cytokine release assays, transcription-based assays, KLRG1/cadherin binding assays, immunological assays other assays as, for example, described in the Examples. The data obtained from the cell culture assays and animal studies can be used in formulating a range of dosage for use in humans. A dose may be formulated in animal models to achieve a circulating plasma concentration range that includes the IC50 (i.e., the concentration of the antibody which achieves a half-maximal inhibition of symptoms). Circulating levels in plasma may be measured, for example, by high performance liquid chromatography. The effects of any particular dosage can be monitored by a suitable bioassay. The dosage lies preferably within a range of circulating concentrations with little or no toxicity. The dosage may vary depending upon the dosage form employed and the route of administration utilized.

The following Examples do not in any way limit the scope of the invention. One of ordinary skill in the art will recognize the numerous modifications and variations that may be performed without altering the spirit or scope of the present invention. Such modifications and variations are encompassed within the scope of the invention. The entire contents of all references, patents, and published patent applications cited throughout this application are herein incorporated by reference.

EXAMPLES

Example 1: Production of Recombinant Proteins

Recombinant proteins were produced by standard molecular cloning and expression protocols include human KLRG1 ECD (SEQ ID NO:89), cynonolgus KLRG1 ECD (SEQ ID NO:90), and human E-cadherin (SEQ ID NO:91), whose amino acid sequences are shown in Table 6, below. Recombinant proteins were produced as FC fusion or as HIS tagged versions by cloning the respective cDNA into pCDNA4 vector (Invitrogen) and transient transfection in mammalian HEK293. Purification of the expressed proteins took place by chromatography using Protein A affinity resin for the FC fusion versions and Nickel-NTA resin for HIS tagged proteins. All purified proteins were characterized by SDS-PAGE electrophoresis to verify purity and molecular weight.

TABLE 6

Amino acid sequences of human and cynomologus KLRG1 ECD and human E-Cadherin

| SEQ ID NO. | Protein | Amino Acid Sequence |
|---|---|---|
| SEQ ID NO: 89 | Human KLRG1 ECD | LCQGSNYSTCASCPSCPDRWMKYGNHCYYFS VEEKDWNSSLEFCLARDSHLLVITDNQEMSL LQVFLSEAFCWIGLRNNSGWRWEDGSPLNFS RISSNSFVQTCGAINKNGLQASSCEVPLHWV CKKVRL |
| SEQ ID NO: 90 | cynomolgus KLRG1 ECD | LCQGSKYSTCASCPSCPDHWMKYGNHCYYFS VEEKDWISSLEFCLARDSHLLMITDKQEMSL LQDFLSEAFHWVGLRNNSGWRWEDGSPLNFS RIYSNSLVQTCGAINKNSLQASSCEVSLQWV CKKVSP |
| SEQ ID NO: 91 | Human E-Cadherin | DWVIPPISCPENEKGPFPKNLVQIKSNKDKE GKVFYSITGQGADTPPVGVFIIERETGWLKV TEPLDRERIATYTLFSHAVSSNGNAVEDPME ILITVTDQNDNKPEFTQEVFKGSVMEGALPG TSVMEVTATDADDDVNTYNAAIAYTILSQDP ELPDKNMFTINRNTGVISVVTTGLDRESFPT YTLVVQAADLQGEGLSTTATAVITVTDTNDN PPIFNPTTYKGQVPENEANVVITTLKVTDAD APNTPAWEAVYTILNDDGGQFVVTTNPVNND GILKTAKGLDFEAKQQYILHVAVTNVVPFEV SLTTSTATVTVDVLDVNEAPIFVPPEKRVEV SEDFGVGQEITSYTAQEPDTFMEQKITYRIW RDTANWLEINPDTGAISTRAELDREDFEHVK NSTYTALIIATDNGSPVATGTGTLLLILSDV NDNAPIPEPRTIFFCERNPKPQVINIIDADL PPNTSPFTAELTHGASANWTIQYNDPTQESI ILKPKMALEVGDYKINLKLMDNQNKDQVTTL EVSVCDCEGAAGVCRKAQPVEAGLQIPAILG ILGGILALLILILLLLFLRRRAVVKEPLLP PEDDTRDNVYYYDEEGGGEEDQDFDLSQLHR GLDARPEVTRNDVAPTLMSVPRYLPRPANPD EIGNFIDENLKAADTDPTAPPYDSLLVFDYE GSGSEAASLSSLNSSESDKDQDYDYLNEWGN RFKKLADMYGGGEDD |

Stable cell lines were developed to be used as immunization antigens, to test binding of antibodies to full length antigen and as target cells in functional T cell assays. Cell lines developed include CHO expressing full length human KLRG1 and CHO expressing full length cynomolgus KLRG1. Stable cell lines were derived by transfection CHO cells with pCDNA4 plasmid coding protein of interest. After transfection, the cells were exposed to 500 ug/ml of G418 to select for stably integrated plasmid. The cell lines were further characterized by FACS for expression and were sorted to select for homogeneous and stable expression.

Stable CHO cells double transfected with CD3 agonist and E-cadherin were used in functional assays for demonstrating the effect of blockage of KLRG1 a human T cells. Co-expression of CD3 agonist and E-cadherin was verified by 2 color FACS with appropriate antibodies.

Example 2: Generation of Anti-KLRG1 Antibodies

Antibodies ABC_HG1N01, ABC_HG1N02 and ABC_HG1N07 are humanized IgG1 antibodies against the extracellular domain of KLRG1. Mouse monoclonal antibodies (MAB) against human KLRG1 was generated by standard immunizations of female BALB/c mice and SJL mice with human and cynomolgus KLRG1, and subsequent hybridoma screening. Several immunization strategies have been employed to generate a diverse number of antibody hits. Briefly SJL and Balb/c mice were repeatedly immunized with either cDNA, recombinant antigen or CHO cells expressing the antigen of interest. Antigen specific antibody titers were periodically monitored by ELISA and animals were sacrificed when appropriate titers were reached, usually between 1:1000 and 1:10000 dilution factor. Splenocytes from sacrificed mice were fused to mouse myeloma cells to produce hybridoma cells and later cultured and sub-cloned into single cells. Stable clones were scaled up and condition media was harvested and tested for expression of anti-KLRG1 antibodies by ELISA and FACS.

Example 3: Selection of Anti-KLRG1 Blocking Antibodies

Hybridoma produced antibodies were screened for binding to human KLRG1 ECD and cynomolgus KRG1 ECD. Antibodies with cross reactivity between both antigens were chosen to move forward to the next stage of screening to determine their ability to neutralize the interaction between KLRG1 and E-cadherin. Antibodies were ranked according to their binding EC50 to human and cyno KLRG1 and further prioritized according to their IC50 in an E-cadherin competition assay. A total of 48 antibodies were selected according to these criteria. Eight antibodies were prioritized for functional characterization in cell-based assay. Table 3 summarizes the variable region amino acid sequences of the 8 mouse antibodies selected and Table 4 shows the CDR regions for the 8 mouse antibodies selected. The antibodies were further ranked according to the presence of sequence liabilities motifs summarized in Table 7. A deamidation site (NG) was found in CDR-L1 of ABC_G1N01 and ABC_G1N02 that could affect stability manufacturability and activity of drug material. In order the remove this potential liability a series of mutants were constructed and tested. Specifically, the NG motif can be substituted with NA, QG and KG sequences without loos of binding. Mouse antibodies can be humanized by grafting the CDR regions into human framework. Table 1 shows examples of variable region sequences of humanized constructs for ABC_GIN01 (ABC_HG1N01), ABC_G1N02 (ABC_HG1N02) and ABC_G1N07 (ABC_HG1N07). Furthermore conservative mutations can be made to the CDR regions to improve affinity, potency or biophysical characteristics. Table 5 summarizes a list of conservative mutations that can be made to the CDR regions. The monoclonal antibodies were epitope binned according to their ability to compete with each other. It was found that antibodies can be grouped in 3 distinct bins; BIN1 includes: ABC_G1N01, ABC_G1N02, ABC_G1N03, ABC_G1N04, ABC_G1N05. BIN2 includes: MAB25, MAB031. BIN3 includes: ABC_G1N07, ABC_G1N08. The antibodies were produced as chimeric by cloning the variable mouse regions onto human IgG constant frameworks and tested in functional assays to determine their functional activity on human T cells and described herein.

TABLE 7

Sequence liability motifs used to screen antibodies for potential manufacturability problems

| Liability | Motif | Consequence |
|---|---|---|
| Unpaired cysteine | C | Adduct formation, activity loss, scrambling, aggregation, process inconsistency |
| Deamidation | NG | Activity loss, aggregation, process inconsistency |
| N-glycosylation | NXS/T, X not P | Impact on PK if heavily sialylated, activity loss |
| Tyrosine sulphation | Neg-Neg-Y-Neg-Neg | Activity loss, process inconsistency |
| Hydrolysis Asp-Pro | DP | Fragmentation, stability |
| Methionine oxidation | M | Activity loss, aggregation |
| Tryptophan oxidation | W | Photosensitivity, activity loss |
| Deamidation | NS, QG, NN | Activity loss, aggregation, process inconsistency |
| Asparatate isomerisation | DG, DS, DQ, DK | Activity loss, aggregation |

Example 4: Characterization of Antibody Binding to KLRG1 (EC50) and Inhibition and KLRG1/E-Cadherin Interaction by FACS (IC50)

Binding of anti-KLRG1 monoclonal antibodies to cell expressed human and cynomolgus-KLRG1 was carried out by FACS. Chinese hamster ovary (CHO) cells were stably transfected to express full length human KLRG1 (CHO-human-KLRG1) and cynomolgus KLRG1 (CHO-cynomolgus-KLRG1). EC50 values were determined by incubation of varying concentrations of anti-KLRG1 monoclonal antibodies at concentrations ranging from 1-100 nM and measuring fluorescence of the labeled cells using an anti-mouse detection antibody directly conjugated with a fluorescent probe.

The ability of monoclonal antibodies to inhibit E-cadherin/KLRG1 binding was measured by FACS. Binding of E-cadherin to CHO-hKLRG1 cells was first determined by incubating the KLRG1 expressing cells with varying concentration of HIS tagged recombinant E-cadherin and detected by FACS with anti-HIS detection antibody. EC50 of E-cadherin/KLRG1 interaction was determined by this method to be 1 µM. IC50 values for each monoclonal antibody was determined by monitoring the loss of E-cadherin binding as a function of varying the concentration of monoclonal antibodies from 0.1 to 100 nM. EC50 and IC50 values are calculated using SigmaPlot software and are summarized in Table 8.

TABLE 8

Binding EC50 and E-cadherin inhibition IC50 of MABs measured by FACS.

| | Binding EC50 (nM) | | E-cadherin inhibition |
|---|---|---|---|
| Antibody ID | Human KLRG1 | Cyno KLRG1 | IC50 (nM) |
| ABC_G1N01 | 1.21 | 1.45 | 12.2 |
| ABC_G1N02 | 1.01 | 2.02 | 5.03 |
| ABC_G1N03 | 1.3 | 1.06 | NA |
| ABC_G1N04 | 29.0 | 0.47 | NA |
| ABC_G1N05 | 39.8 | 0.5 | 23 |
| ABC_G1N06 | 1.43 | 1.5 | 41 |
| MAB031 | 5.1 | 5.93 | 39 |
| ABC_G1N07 | 0.94 | 0.98 | 9.6 |
| ABC_G1N08 | 4.8 | 1.3 | 10 |

Example 5: Measurement of Binding Kinetics

Binding kinetics of humanized antibodies for human and cynomolgus KLRG1 were determined by OCTET® measurement. OCTET® Systems use Bio-Layer Interferometry (BLI) technology to monitor the binding of proteins and other biomolecules to their partners directly in real time, providing analysis of kinetic binding constants. See https.//www.fortebio.com/bli-technology.html, the contents of which, including all links and sublinks associated therewith, is incorporated by reference herein in its entirety. The experimental set-up consists of immobilizing biotinylated recombinant antigen (Human-KLRG-ECD or cynomolgus-KLRG1-ECD) on streptavidin OCTET® sensor to produce antigen loaded sensors. The loaded sensors are the exposed to varying concentrations of each humanized antibody from 100 to 0.1 nM in the OCTET® instruments and data collected for 600 seconds to measure association kinetic ($K_{on}$) of the antibody/antigen complex. In a following step the sensors are exposed to a solution of 1× phosphate buffered saline (PBS) buffer devoid of antibody for 600 seconds to observe dissociation kinetics ($K_{off}$). The resulting data is then fitted to 1:1 binding kinetics model using ForteBio® analysis software to calculate the $K_D$. Kinetic binding parameters derived by this method are summarized in Table 9 for the three humanized antibodies.

TABLE 9

Binding affinity of selected MABs measured by OCTET ®:

| Antigen | Antibody | $K_{on}$ (1/Ms) | $K_{off}$ (1/s) | $K_D$ (M) |
|---|---|---|---|---|
| Human KLRG1 | ABC_G1N01 | 2.29E+06 | 2.87E−04 | 1.25E−10 |
| | ABC_G1N02 | 2.80E+06 | 6.81E−04 | 2.43E−10 |
| | ABC_G1N07 | 1.97E+06 | <1.0E−05 | <5.1E−12 |
| Cyno KLRG1 | ABC_G1N01 | 6.64E+05 | 4.10E−05 | 6.17E−11 |
| | ABC_G1N02 | 6.30E+05 | 4.07E−05 | 6.47E−11 |
| | ABC_G1N07 | 8.80E+05 | 1.25E−03 | 1.42E−09 |

Example 6: Characterization of Functional Activity for KLRG1 Blocking Antibodies Blocking KLRG1 interaction with its ligands has an activating effect on human CD8+ T cell by measuring the effect of antibody mediated blockade on KLRG1 signaling on production of IFNγ and on the proliferation of T cells (Proliferation index). To demonstrate the effect of KLRG1 blockade on cells of the immune system, CD8+ T cells were isolated from healthy donors and tested in co-culture with a CHO cell line co-expressing a CD3 agonist and a E-cadherin (eAPC). The assay works by providing T cells with 2 competing signals where CD3 stimulation is counteracted by the inhibitory effect of E-cadherin. When KLRG1 signaling is blocked by anti-KLRG1 antibodies, the inhibitory signal is disrupted, and T cells are activated according to their interaction with the CD3 agonist expressed on the cell surface. IFNγ secretion is measured by ELISA and results summarized in Table 10 and FIG. 1.

TABLE 10

Restoration of IFNγ Release by KLRG1 blocking antibodies in Human CD8+ T cells

| | IFNγ released (pg/ml) | |
|---|---|---|
| | Sample 1 | Sample 2 |
| CD8 positive control | 1624.09 | 1401.42 |
| Isotype | 390.02 | 355.94 |
| ABC_G1N07 | 1579.71 | 1389.6 |
| ABC_G1N02 | 1440.87 | 1290.52 |
| ABC_G1N01 | 1185.14 | 1217.73 |
| ABC_G1N06 | 1023.15 | 1142.09 |
| ABC_G1N05 | 1012.46 | 1083.04 |
| ABC_G1N08 | 1013.8 | 1063.23 |
| CD8 positive control | 1624.09 | 1401.42 |
| ABC_G1N04 | 987.48 | 1002.46 |
| ABC_G1N03 | 934.34 | 868.9 |

This data demonstrate that E-cadherin has an inhibiting effect on human T cells which can be reversed by blockade of KLRG1 signaling with blocking antibodies.

Figure 2:
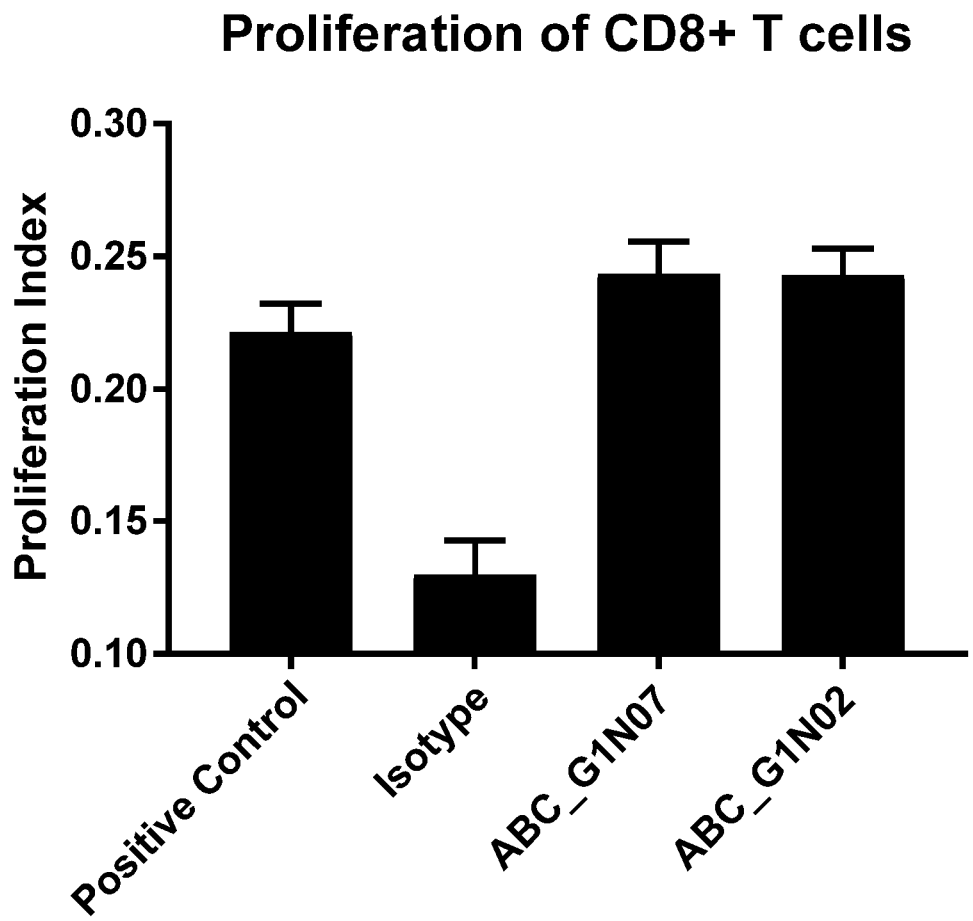
FIG. 2 shows result of a CD8+ T cell proliferation assay demonstrating that anti-KLRG1 antibodies induce proliferation of CD8+ T cells.

The data presented in Table 11 and FIG. 2 demonstrates that blocking of KLRG1/E-cadherin interaction results in proliferation of human CD8+ T cells by measuring the proliferation index in response to eAPC. In this assay eAPC were produced by stably transducing CHO cells with h-Ec-adherin and an CD3 agonist agent. The eAPC thus produced were then co-incubated for 3 days with freshly isolated CD8+ T cells from a healthy volunteer in the presence of 10 micro-gram/ml of test antibodies or isotype control. The positive control sample was prepared by incubating CD8+ T cells with CHO cells stably expressing anti-CD3 but lacking expression of inhibitory ligand E-cadherin, thus allowing un-inhibited stimulation of CD8+ T cell by anti-CD3 expressed on CHO cells. The results show that CD8+ T cells proliferate in response to CD3 stimulation as expected and that the inhibitory ligand E-cadherin co-expression on eAPC inhibits proliferation of CD8+ T cells. Furthermore, CD8+ T cell proliferation can be restored by blockade of KLRG1 by neutralizing antibodies.

TABLE 11

Effect of KLRG1 blockage on CD8+ T cell proliferation

| | Division Index | |
|---|---|---|
| Positive Control | 0.214 | 0.229 |
| Isotype | 0.139 | 0.121 |
| ABC_G1N07 | 0.252 | 0.235 |
| ABC_G1N02 | 0.25 | 0.236 |

Figure 3:
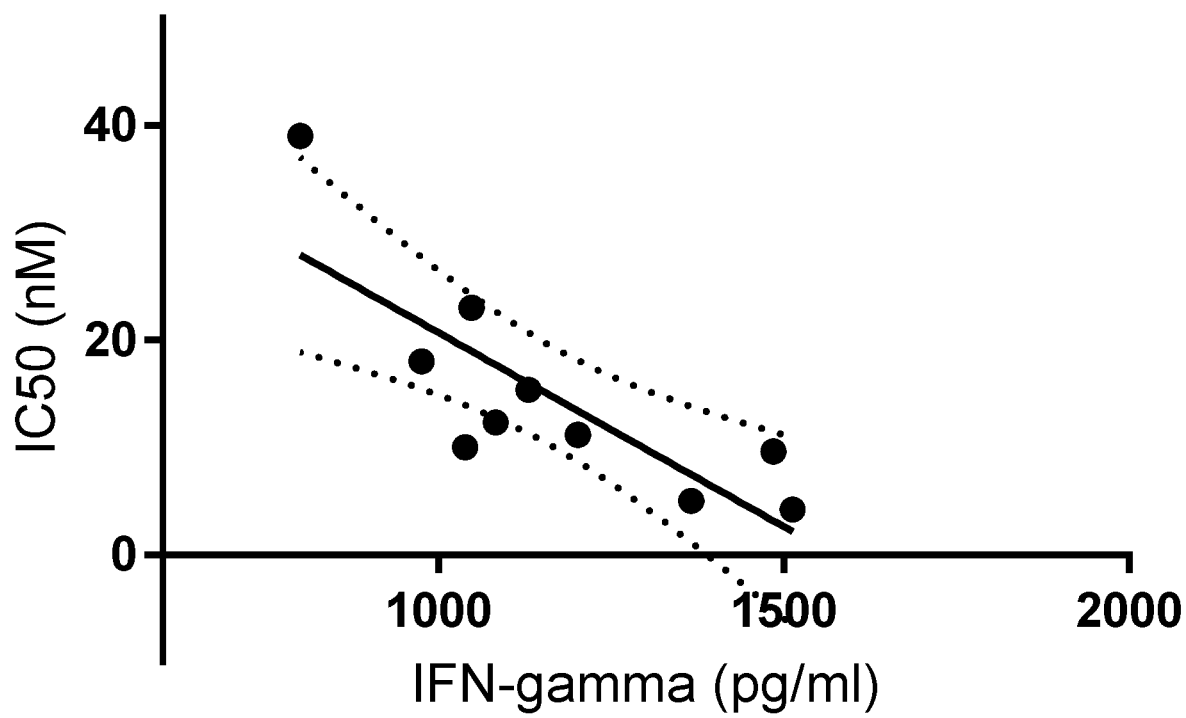
FIG. 3 shows relationship between the results of an IFNγ secretion assay in CD8+ T cells treated with anti-KLRG1 antibodies and blocking activities (shown in IC50) of the antibodies.

The data presented in Table 12 and FIG. 3 shows the correlation between T cell activity in the IFNγ secretion assay and blocking activity of anti-KLRG1 neutralizer antibodies. IC50 values for each antibody were derived from E-cadherin binding inhibition studies and plotted against IFNγ production levels measured in CD8+ T cells IFNγ release assays. The correlation shows that antibodies with lower IC50 values (e.g. more potent blockers of KLRG1/E-cadherin binding) result in higher levels of IFNγ release by CD8+ T cells. This data demonstrates that antibody blockade of KLRG1 results in restoration of T cell activity in an E-cadherin dependent manner.

TABLE 12

Correlation between E-cadherin IC50 competition values and IFNγ Secretion

| mAb | IFNγ (pg/ml) | IC50 (nM) |
|---|---|---|
| ABC_G1N07 | 1512.76 | 4.21 |
| ABC_G1N02 | 1484.66 | 9.6 |
| ABC_G1N01 | 1365.7 | 5 |
| MAB034 | 1201.44 | 11.2 |
| MAB024 | 1129.8 | 15.4 |
| ABC_G1N05 | 1082.62 | 12.3 |
| ABC_G1N08 | 1047.75 | 23 |
| MAB036 | 1038.52 | 10 |
| MAB031 | 975.34 | 18 |
| Isotype | 799.27 | 39 |

What is claimed is:

1. An antibody, or antigen binding fragment thereof, comprising:

(a) a heavy chain variable (VH) domain comprising complementarity-determining regions (CDRs) of CDR-H1, CDR-H2, and CDR-H3 consisting of the amino acid sequences of SEQ ID NOs: 13, 14, and 15, respectively; and (b) a light chain variable (VL) domain comprising a CDR-L2 and CDR-L3 consisting of the amino acid sequences of SEQ ID NO: 17 and SEQ ID NO: 18, respectively and a CDR-L1 consisting of the amino acid sequence of SEQ ID NO: 16 or the amino acid sequence of SEQ ID NO: 16 wherein NG is substituted with NA, QG, or KG;

wherein said antibody, or antigen binding fragment thereof, specifically binds to the extracellular domain of human killer cell lectin-like receptor subfamily G member 1 (KLRG1) and the extracellular domain of cynomolgus monkey KLRG1.

2. The antibody, or antigen binding fragment thereof, of claim 1, wherein CDR-L1 (SEQ ID NO: 16) has NG substituted with NA.

3. The antibody, or antigen binding fragment thereof, of claim 1, comprising:

(i) the VH domain sequence of SEQ ID NO: 3 and the VL domain sequence of SEQ ID NO: 4, or the VL domain sequence of SEQ ID NO:4, wherein NG is substituted with NA in the CDR-L1; or (ii) the VH domain sequence of SEQ ID NO: 27 and the VL domain sequence of SEQ ID NO: 28, or the VL domain sequence of SEQ ID NO:28, wherein NG is substituted with NA in the CDR-L1.

4. The antibody, or antigen binding fragment thereof of claim 1, wherein the antibody specifically binds to an amino acid sequence that is at least one amino acid sequence selected from group consisting of SEQ ID NO: 89 and SEQ ID NO: 90.

5. The antibody, or antigen binding fragment thereof, of claim 1, wherein the antibody specifically binds to the extracellular domain of KLRG1 with an affinity, as expressed in $K_D$, of at least 2 nM, 1 nM, 100 pM, 10 pM, or 5 pM.

6. The antibody, or antigen binding fragment thereof of claim 1, wherein the antibody is humanized.

7. The antibody, or antigen binding fragment thereof of claim 1, wherein the antibody is IgG1 or IgG4.

8. A pharmaceutical composition comprising the antibody or antigen binding fragment thereof of claim 1 and a pharmaceutically acceptable carrier.

9. An antibody, or antigen binding fragment thereof, comprising:
(a) a heavy chain variable (VH) domain comprising complementarity-determining regions (CDRs) of CDR-H1, CDR-H2, and CDR-H3 consisting of the amino acid sequences of SEQ ID NOs: 7, 8, and 9, respectively; and
(b) a light chain variable (VL) domain comprising a CDR-L2 and CDR-L3 consisting of the amino acid sequences of SEQ ID NO: 11 and SEQ ID NO: 12, respectively and a CDR-L1 consisting of the amino acid sequence of SEQ ID NO: 10 or the amino acid sequence of SEQ ID NO: 10 wherein NG is substituted with NA, QG, or KG;

wherein said antibody, or antigen binding fragment thereof, specifically binds to the extracellular domain of human killer cell lectin-like receptor subfamily G member 1 (KLRG1) and the extracellular domain of cynomolgus monkey KLRG1.

10. The antibody, or antigen binding fragment thereof, of claim 9, wherein CDR-L1 (SEQ ID NO: 10) has NG substituted with NA.

11. The antibody, or antigen binding fragment thereof, of claim 9, comprising:
(i) the VH domain sequence of SEQ ID NO: 1 and the VL domain sequence of SEQ ID NO: 2, or the VL domain sequence of SEQ ID NO: 2, wherein NG is substituted with NA in the CDR-L1; or
(ii) the VH domain sequence of SEQ ID NO: 25 and the VL domain sequence of SEQ ID NO: 26, or the VL domain sequence of SEQ ID NO: 26, wherein NG is substituted with NA in the CDR-L1.

12. The antibody, or antigen binding fragment thereof of claim 9, wherein the antibody specifically binds to an amino acid sequence that is at least one amino acid sequence selected from group consisting of SEQ ID NO: 89 and SEQ ID NO: 90.

13. The antibody, or antigen binding fragment thereof, of claim 9, wherein the antibody specifically binds to the extracellular domain of KLRG1 with an affinity, as expressed in $K_D$, of at least 2 nM, 1 nM, 100 pM, 10 pM, or 5 pM.

14. The antibody, or antigen binding fragment thereof of claim 9, wherein the antibody is humanized.

15. The antibody, or antigen binding fragment thereof of claim 9, wherein the antibody is IgG1 or IgG4.

16. A pharmaceutical composition comprising the antibody or antigen binding fragment thereof of claim 9 and a pharmaceutically acceptable carrier.

\* \* \* \* \*

SEQUENCE LISTING

```
<160> NUMBER OF SEQ ID NOS: 91

<210> SEQ ID NO 1
<211> LENGTH: 125
<212> TYPE: PRT
<213> ORGANISM: Artificial Sequence
<220> FEATURE:
<223> OTHER INFORMATION: Humanized mouse antibody partial sequence

<400> SEQUENCE: 1

Gln Val Ile Leu Lys Glu Ser Gly Pro Gly Leu Val Lys Pro Thr Gln
1               5                   10                  15

Thr Leu Thr Leu Thr Cys Thr Phe Ser Gly Phe Ser Leu Thr Thr Phe
            20                  25                  30

Gly Met Gly Ile Gly Trp Ile Arg Gln Pro Pro Gly Lys Ala Leu Glu
        35                  40                  45

Trp Leu Ala His Ile Trp Trp Asn Asp Asp Lys Ser Tyr Asn Ser Ala
    50                  55                  60

Leu Lys Ser Arg Leu Thr Ile Ser Lys Asp Thr Ser Lys Asn Gln Val
65                  70                  75                  80
```

```
Val Leu Thr Met Thr Asn Met Asp Pro Val Asp Ala Thr Tyr Tyr
                85                  90                  95

Cys Ala Arg Thr Ile Tyr Tyr Gly Asn Tyr Leu Thr Phe Tyr Ala Met
            100                 105                 110

Glu His Trp Gly Gln Gly Thr Thr Val Thr Val Ser Ser
            115                 120                 125

<210> SEQ ID NO 2
<211> LENGTH: 115
<212> TYPE: PRT
<213> ORGANISM: Artificial Sequence
<220> FEATURE:
<223> OTHER INFORMATION: Humanized mouse antibody partial sequence

<400> SEQUENCE: 2

Asp Ile Leu Met Thr Gln Ser Pro Leu Ser Leu Pro Val Thr Pro Gly
1               5                   10                  15

Glu Pro Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Pro Thr Phe Gly Ala Gly Thr Lys Leu Glu Leu Lys
            100                 105                 110

Arg Thr Val
        115

<210> SEQ ID NO 3
<211> LENGTH: 125
<212> TYPE: PRT
<213> ORGANISM: Artificial Sequence
<220> FEATURE:
<223> OTHER INFORMATION: Humanized mouse antibody partial sequence

<400> SEQUENCE: 3

Gln Val Thr Leu Lys Glu Ser Gly Pro Gly Leu Val Lys Pro Thr Gln
1               5                   10                  15

Thr Leu Thr Leu Thr Cys Thr Phe Ser Gly Phe Ser Leu Ser Thr Phe
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Trp Tyr Glu Leu Ala
    50                  55                  60

Leu Lys Ser Arg Leu Thr Ile Ser Lys Asp Ser Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Ile Tyr Tyr Gly Ser Arg Ser Ala Tyr Ser Met
            100                 105                 110

Asp Tyr Trp Gly Pro Gly Thr Thr Val Thr Val Ser Ser
        115                 120                 125

<210> SEQ ID NO 4
```

```
<211> LENGTH: 115
<212> TYPE: PRT
<213> ORGANISM: Artificial Sequence
<220> FEATURE:
<223> OTHER INFORMATION: Humanized mouse antibody partial sequence

<400> SEQUENCE: 4

Asp Ile Leu Met Thr Gln Ser Pro Leu Ser Leu Pro Val Thr Pro Gly
1               5                   10                  15

Glu Pro Ala Ser Ile Ser Cys Lys Ser Gln Ser Val His Ser
            20                  25                  30

Asn Gly His Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Val Thr Phe Gly Ala Gly Thr Lys Leu Glu Leu Lys
            100                 105                 110

Arg Thr Val
        115

<210> SEQ ID NO 5
<211> LENGTH: 119
<212> TYPE: PRT
<213> ORGANISM: Artificial Sequence
<220> FEATURE:
<223> OTHER INFORMATION: Humanized mouse antibody partial sequence

<400> SEQUENCE: 5

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Ile Arg Gln Thr Pro Gly Lys Gly Leu Glu Trp Val
        35                  40                  45

Ala Thr Ile Ser Glu Ser Gly Asn Tyr Asn Tyr Pro Asp Asn Val
    50                  55                  60

Lys Gly Arg Leu Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Val Arg Asp Asp Trp Glu Gly Arg Ala Met Asp Tyr Trp Gly Gln Gly
            100                 105                 110

Thr Thr Val Thr Val Ser Ser
        115

<210> SEQ ID NO 6
<211> LENGTH: 110
<212> TYPE: PRT
<213> ORGANISM: Artificial Sequence
<220> FEATURE:
<223> OTHER INFORMATION: Humanized mouse antibody partial sequence

<400> SEQUENCE: 6

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Arg Asp Ile Gly Ser Ser
             20                  25                  30

Leu Asn Trp Tyr Gln Gln Lys Pro Gly Gly Ala Pro Lys Arg Leu Ile
         35                  40                  45

Tyr Ala Thr Ser Ser Leu Asp Ser Gly Val Pro Lys Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Thr Tyr Tyr Cys Leu Gln Tyr Ala Ser Ser Pro Trp
                 85                  90                  95

Thr Phe Gly Gln Gly Thr Lys Val Glu Ile Lys Arg Thr Val
            100                 105                 110
```

<210> SEQ ID NO 7
<211> LENGTH: 9
<212> TYPE: PRT
<213> ORGANISM: Artificial Sequence
<220> FEATURE:
<223> OTHER INFORMATION: Humanized mouse antibody partial sequence

<400> SEQUENCE: 7

```
Gly Phe Ser Leu Thr Thr Phe Gly Met
 1               5
```

<210> SEQ ID NO 8
<211> LENGTH: 5
<212> TYPE: PRT
<213> ORGANISM: Artificial Sequence
<220> FEATURE:
<223> OTHER INFORMATION: Humanized mouse antibody partial sequence

<400> SEQUENCE: 8

```
Trp Trp Asn Asp Asp
 1               5
```

<210> SEQ ID NO 9
<211> LENGTH: 15
<212> TYPE: PRT
<213> ORGANISM: Artificial Sequence
<220> FEATURE:
<223> OTHER INFORMATION: Humanized mouse antibody partial sequence

<400> SEQUENCE: 9

```
Thr Ile Tyr Tyr Gly Asn Tyr Leu Thr Phe Tyr Ala Met Glu His
 1               5                  10                  15
```

<210> SEQ ID NO 10
<211> LENGTH: 16
<212> TYPE: PRT
<213> ORGANISM: Artificial Sequence
<220> FEATURE:
<223> OTHER INFORMATION: Humanized mouse antibody partial sequence

<400> SEQUENCE: 10

```
Arg Ser Ser Gln Asn Ile Val His Ser Asn Gly Asn Thr Tyr Leu Glu
 1               5                  10                  15
```

<210> SEQ ID NO 11
<211> LENGTH: 7
<212> TYPE: PRT
<213> ORGANISM: Artificial Sequence
<220> FEATURE:
<223> OTHER INFORMATION: Humanized mouse antibody partial sequence

<400> SEQUENCE: 11

```
Lys Val Ser Asn Arg Phe Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Humanized mouse antibody partial sequence

<400> SEQUENCE: 12

Phe Gln Gly Ser His Val Pro Pro Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Humanized mouse antibody partial sequence

<400> SEQUENCE: 13

Gly Phe Ser Leu Ser Thr Phe Gly Met
1               5

<210> SEQ ID NO 14
<211> LENGTH: 5
<212> TYPE: PRT
<213> ORGANISM: Artificial Sequence
<220> FEATURE:
<223> OTHER INFORMATION: Humanized mouse antibody partial sequence

<400> SEQUENCE: 14

Trp Trp Asp Asp Asp
1               5

<210> SEQ ID NO 15
<211> LENGTH: 15
<212> TYPE: PRT
<213> ORGANISM: Artificial Sequence
<220> FEATURE:
<223> OTHER INFORMATION: Humanized mouse antibody partial sequence

<400> SEQUENCE: 15

Val Ile Tyr Tyr Gly Ser Arg Ser Ala Tyr Tyr Ser Met Asp Tyr
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Humanized mouse antibody partial sequence

<400> SEQUENCE: 16

Lys Ser Ser Gln Ser Ile Val His Ser Asn Gly His Thr Tyr Leu Glu
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: Humanized mouse antibody partial sequence

<400> SEQUENCE: 17
```

Lys Val Ser Asn Arg Phe Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Humanized mouse antibody partial sequence

<400> SEQUENCE: 18

Phe Gln Gly Ser His Val Pro Val Thr
1               5

<210> SEQ ID NO 19
<211> LENGTH: 7
<212> TYPE: PRT
<213> ORGANISM: Artificial Sequence
<220> FEATURE:
<223> OTHER INFORMATION: Humanized mouse antibody partial sequence

<400> SEQUENCE: 19

Gly Phe Thr Phe Arg Asn Tyr
1               5

<210> SEQ ID NO 20
<211> LENGTH: 6
<212> TYPE: PRT
<213> ORGANISM: Artificial Sequence
<220> FEATURE:
<223> OTHER INFORMATION: Humanized mouse antibody partial sequence

<400> SEQUENCE: 20

Ser Glu Ser Gly Asn Tyr
1               5

<210> SEQ ID NO 21
<211> LENGTH: 10
<212> TYPE: PRT
<213> ORGANISM: Artificial Sequence
<220> FEATURE:
<223> OTHER INFORMATION: Humanized mouse antibody partial sequence

<400> SEQUENCE: 21

Asp Asp Trp Glu Gly Arg Ala Met Asp Tyr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Humanized mouse antibody partial sequence

<400> SEQUENCE: 22

Arg Ala Ser Arg Asp Ile Gly Ser Ser Leu Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Humanized mouse antibody partial sequence

<400> SEQUENCE: 23

Ala Thr Ser Ser Leu Asp Ser

<210> SEQ ID NO 24
<211> LENGTH: 9
<212> TYPE: PRT
<213> ORGANISM: Artificial Sequence
<220> FEATURE:
<223> OTHER INFORMATION: Humanized mouse antibody partial sequence

<400> SEQUENCE: 24

Leu Gln Tyr Ala Ser Ser Pro Trp Thr
1               5

<210> SEQ ID NO 25
<211> LENGTH: 125
<212> TYPE: PRT
<213> ORGANISM: Mus musculus

<400> SEQUENCE: 25

Gln Val Ile Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Phe
            20                  25                  30

Gly Met Gly Ile Gly Trp Ile Arg His Pro Ser Gly Lys Ala Leu Glu
        35                  40                  45

Trp Leu Ala His Ile Trp Trp Asn Asp Lys Ser Tyr Asn Ser Ala
    50                  55                  60

Leu Lys Ser Arg Leu Thr Ile Ser Lys Asp Thr Ser Lys Asn Gln Val
65                  70                  75                  80

Phe Leu Arg Leu Ala Asn Val Ala Thr Ala Asp Thr Ala Thr Tyr Tyr
                85                  90                  95

Cys Ala Arg Thr Ile Tyr Tyr Gly Asn Tyr Leu Thr Phe Tyr Ala Met
            100                 105                 110

Glu His Trp Gly Gln Gly Thr Ser Val Thr Val Ser Ser
        115                 120                 125

<210> SEQ ID NO 26
<211> LENGTH: 112
<212> TYPE: PRT
<213> ORGANISM: Mus musculus

<400> SEQUENCE: 26

Asp Val Leu Leu Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Leu Lys Pro Gly Gln Ser
        35                  40                  45

Pro Lys Leu Leu Ile Phe Lys Val Ser Asn Arg Phe Ser Gly Val Pro
    50                  55                  60

Asp Lys Phe Ser Gly Ser Gly Ser Gly Thr Asp Phe Thr Leu Lys Ile
65                  70                  75                  80

Arg Arg Val Glu Ala Glu Asp Leu Gly Ile Tyr Tyr Cys Phe Gln Gly
                85                  90                  95

Ser His Val Pro Pro Thr Phe Gly Ala Gly Thr Lys Leu Glu Leu Lys
            100                 105                 110

<210> SEQ ID NO 27
<211> LENGTH: 125

<212> TYPE: PRT
<213> ORGANISM: Mus musculus

<400> SEQUENCE: 27

Gln Val Thr Leu Lys Glu Ser Gly Pro Gly Ile Leu Gln Pro Ser Gln
1               5                   10                  15

Thr Leu Ser Leu Thr Cys Ser Val Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Trp Tyr Glu Leu Ala
    50                  55                  60

Leu Lys Ser Arg Leu Thr Ile Ser Lys Asp Ser Ser Lys Asn Gln Val
65                  70                  75                  80

Phe Leu Lys Ile Ala Asn Val Asp Thr Ala Asp Thr Ala Thr Tyr Phe
                85                  90                  95

Cys Ala Arg Val Ile Tyr Tyr Gly Ser Arg Ser Ala Tyr Tyr Ser Met
            100                 105                 110

Asp Tyr Trp Gly Pro Gly Thr Ser Val Thr Val Ser Ser
            115                 120                 125

<210> SEQ ID NO 28
<211> LENGTH: 112
<212> TYPE: PRT
<213> ORGANISM: Mus musculus

<400> SEQUENCE: 28

Asp Val Leu Met Thr Gln Thr Pro Leu Ser Leu Pro Val Ser Leu Gly
1               5                   10                  15

Ala Gln Ala Ser Ile Ser Cys Lys Ser Ser Gln Ser Ile Val His Ser
            20                  25                  30

Asn Gly His Thr Tyr Leu Glu Trp Tyr Leu Gln Lys Pro Gly Gln Ser
        35                  40                  45

Pro Lys Ile Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Val Thr Phe Gly Ala Gly Thr Lys Leu Glu Leu Lys
            100                 105                 110

<210> SEQ ID NO 29
<211> LENGTH: 119
<212> TYPE: PRT
<213> ORGANISM: Mus musculus

<400> SEQUENCE: 29

Gln Val His Leu Gln Gln Ser Gly Pro Glu Leu Val Lys Pro Gly Ala
1               5                   10                  15

Ser Val Lys Leu Ser Cys Lys Ala Ser Gly Asp Thr Phe Thr Thr Tyr
            20                  25                  30

Asp Ile Thr Trp Val Lys Gln Arg Pro Gly Gln Gly Leu Glu Trp Ile
        35                  40                  45

Gly Trp Ile Tyr Pro Lys Asp Gly Arg Thr Gln Asn Ser Glu Lys Phe
    50                  55                  60

Lys Asp Lys Ala Thr Leu Thr Val Asp Thr Ser Ser Thr Thr Ala Tyr

-continued

```
            65                  70                  75                  80
Met Glu Leu His Ser Leu Thr Ser Glu Asp Ser Ala Val Tyr Phe Cys
                        85                  90                  95

Ala Arg Arg Gly Gln Phe Gly Pro Tyr Phe Asp His Trp Gly Gln Gly
                100                 105                 110

Ser Thr Leu Thr Val Ser Ser
            115
```

<210> SEQ ID NO 30
<211> LENGTH: 107
<212> TYPE: PRT
<213> ORGANISM: Mus musculus

<400> SEQUENCE: 30

```
Val Ile Gln Met Thr Gln Ser Ser Phe Leu Ser Ala Ser Leu Gly
1               5                   10                  15

Gly Arg Val Ser Ile Thr Cys Arg Ala Ser Asp His Ile Tyr Asn Trp
                20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Ile Pro Ser Arg Phe Ser Gly
        50                  55                  60

Gly Gly Ser Gly Lys Asp Tyr Thr Leu Thr Ile Ser Leu Gln Thr
65                  70                  75                  80

Glu Asp Ile Ala Ser Tyr Tyr Cys Gln Gln Tyr Trp Asn Thr Pro Pro
                85                  90                  95

Thr Phe Gly Gly Gly Thr Lys Val Glu Ile Lys
                100                 105
```

<210> SEQ ID NO 31
<211> LENGTH: 122
<212> TYPE: PRT
<213> ORGANISM: Mus musculus

<400> SEQUENCE: 31

```
Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Ser Phe Ser Thr Phe
                20                  25                  30

Gly Met His Trp Val Arg Gln Val Pro Glu Lys Gly Leu Glu Trp Val
            35                  40                  45

Ala Tyr Ile Ser Ser Gly Ser Tyr Ser Ile Phe Tyr Ala Asp Ser Val
        50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Ile Tyr Tyr Cys
                85                  90                  95

Thr Arg Thr Arg Asp Ser Gly Ser Pro His Tyr Phe Asp Tyr Trp
                100                 105                 110

Gly Gln Gly Thr Thr Val Thr Val Ser Ser
            115                 120
```

<210> SEQ ID NO 32
<211> LENGTH: 111
<212> TYPE: PRT
<213> ORGANISM: Mus musculus

<400> SEQUENCE: 32

Asp Ile Val Leu Thr Gln Ser Pro Thr Ser Leu Ala Val Ser Leu Gly
1               5                   10                  15

Gln Arg Ala Thr Ile Ser Cys Arg Ala Ser Lys Ser Val Asp Ser Tyr
            20                  25                  30

Gly Ile Ser Phe Met Asn Trp Phe Gln Gln Lys Pro Gly Gln Ser Pro
        35                  40                  45

Lys Leu Leu Ile Tyr Gly Ala Ser Asn Arg Gly Ser Gly Val Pro Ala
    50                  55                  60

Arg Phe Ser Gly Ser Gly Ser Gly Thr Asp Phe Ser Leu Asn Ile His
65              70                  75                  80

Pro Met Glu Glu Asp Asp Thr Ala Met Tyr Phe Cys Gln Gln Ser Lys
                85                  90                  95

Glu Gly Pro Phe Thr Phe Gly Thr Gly Thr Lys Leu Glu Leu Arg
            100                 105                 110

<210> SEQ ID NO 33
<211> LENGTH: 123
<212> TYPE: PRT
<213> ORGANISM: Mus musculus

<400> SEQUENCE: 33

Glu Val Leu Leu Met Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Asp Met Ser Trp Val Arg Gln Thr Pro Asp Lys Arg Leu Glu Trp Val
        35                  40                  45

Ala Thr Ile Ser Ser Ser Gly Arg Tyr Thr Phe Tyr Pro Asp Asn Val
    50                  55                  60

Lys Gly Arg Phe Thr Ile Ser Arg Asp Asn Ala Lys Asn Thr Leu Tyr
65              70                  75                  80

Leu Gln Val Ser Asn Leu Lys Ser Glu Asp Thr Ala Met Tyr Tyr Cys
                85                  90                  95

Ser Arg Thr Gly Val Thr Thr Val Val Phe Thr Asp Tyr Phe Asp Tyr
            100                 105                 110

Trp Gly Gln Gly Thr Thr Leu Thr Val Ser Ser
        115                 120

<210> SEQ ID NO 34
<211> LENGTH: 107
<212> TYPE: PRT
<213> ORGANISM: Mus musculus

<400> SEQUENCE: 34

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Asn Ser
            20                  25                  30

Leu Asn Trp Leu Gln Gln Gly Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Thr Tyr Ser Leu Thr Ile Ser Ser Leu Glu Ser
65              70                  75                  80

Glu Asp Phe Val Ala Tyr Tyr Cys Leu Gln Tyr Leu Ser Ser Pro Pro
                85                  90                  95

```
Thr Phe Gly Gly Gly Thr Lys Leu Glu Ile Lys
                100                 105
```

```
<210> SEQ ID NO 35
<211> LENGTH: 116
<212> TYPE: PRT
<213> ORGANISM: Mus musculus

<400> SEQUENCE: 35

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr His
                20                  25                  30

Ala Val His Trp Val Arg Gln Ser Pro Gly Lys Gly Leu Asp Trp Leu
            35                  40                  45

Gly Val Ile Trp Ser Gly Gly Asn Thr Asp Tyr Asn Ala Ala Phe Ile
        50                  55                  60

Ser Arg Leu Thr Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Val
                85                  90                  95

Arg Leu Leu Leu Pro Ala Met Asp Tyr Trp Gly Gln Gly Thr Ser Val
                100                 105                 110

Thr Val Ser Ser
        115
```

```
<210> SEQ ID NO 36
<211> LENGTH: 108
<212> TYPE: PRT
<213> ORGANISM: Mus musculus

<400> SEQUENCE: 36

Gln Ile Val Leu Thr Gln Ser Pro Ala Ile Met Ser Ala Ser Leu Gly
1               5                   10                  15

Glu Arg Val Thr Met Thr Cys Thr Ala Thr Ser Ser Val Ser Ser Thr
                20                  25                  30

Tyr Leu His Trp Tyr Arg Gln Lys Pro Gly Ser Ser Pro Lys Leu Trp
            35                  40                  45

Ile Tyr Ser Thr Ser Thr Leu Ala Ser Gly Val Pro Val Arg Phe Arg
        50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr Arg Arg Ser Pro
                85                  90                  95

Tyr Thr Phe Gly Gly Gly Thr Lys Leu Glu Ile Lys
                100                 105
```

```
<210> SEQ ID NO 37
<211> LENGTH: 119
<212> TYPE: PRT
<213> ORGANISM: Mus musculus

<400> SEQUENCE: 37

Glu Val Gln Leu Val Glu Ser Gly Gly Gly Leu Val Lys Pro Gly Gly
1               5                   10                  15

Ser Leu Lys Leu Ser Cys Thr Ala Ser Gly Phe Thr Phe Arg Asn Tyr
                20                  25                  30
```

```
Ala Met Ser Trp Val Arg Gln Thr Pro Glu Lys Arg Leu Glu Trp Val
            35                  40                  45
Ala Thr Ile Ser Glu Ser Gly Asn Tyr Asn Tyr Pro Asp Asn Val
 50                  55                  60
Lys Gly Arg Leu Thr Ile Ser Arg Asp Asn Ala Lys Asn Asn Leu Tyr
 65                  70                  75                  80
Leu Gln Met Ser Leu Leu Lys Ser Glu Asp Thr Ala Met Tyr Tyr Cys
                 85                  90                  95
Val Arg Asp Asp Trp Glu Gly Arg Ala Met Asp Tyr Trp Gly Gln Gly
                100                 105                 110
Thr Ser Val Thr Val Ser Ser
            115
```

<210> SEQ ID NO 38
<211> LENGTH: 107
<212> TYPE: PRT
<213> ORGANISM: Mus musculus

<400> SEQUENCE: 38

```
Gly Ile Gln Met Thr Gln Ser Pro Ser Ser Leu Ser Ala Ser Leu Gly
 1               5                  10                  15
Glu Arg Val Ser Leu Thr Cys Arg Ala Ser Arg Asp Ile Gly Ser Ser
                 20                  25                  30
Leu Asn Trp Leu Gln Gln Lys Pro Asp Gly Thr Ile Lys Arg Leu Ile
             35                  40                  45
Tyr Ala Thr Ser Ser Leu Asp Ser Gly Val Pro Lys Arg Phe Ser Gly
 50                  55                  60
Ser Arg Ser Gly Thr Asp Tyr Ser Leu Thr Ile Ser Ser Leu Glu Ser
 65                  70                  75                  80
Glu Asp Phe Val Asp Tyr Phe Cys Leu Gln Tyr Ala Ser Ser Pro Trp
                 85                  90                  95
Thr Phe Gly Gly Gly Thr Lys Leu Glu Ile Lys
                100                 105
```

<210> SEQ ID NO 39
<211> LENGTH: 119
<212> TYPE: PRT
<213> ORGANISM: Mus musculus

<400> SEQUENCE: 39

```
Gln Val Gln Leu Gln Gln Ser Gly Ala Glu Leu Ala Lys Pro Gly Ala
 1               5                  10                  15
Ser Val Lys Leu Ser Cys Lys Ala Ser Gly Tyr Thr Phe Thr Ser Tyr
                 20                  25                  30
Phe Leu His Trp Val Lys Gln Arg Pro Gly Gln Gly Leu Glu Trp Ile
             35                  40                  45
Gly Tyr Met Asn Pro Ser Ser Gly Tyr Thr Lys Cys Asn Gln Lys Phe
 50                  55                  60
Lys Asp Lys Ala Thr Leu Thr Ala Asp Lys Ser Ser Thr Ala Tyr
 65                  70                  75                  80
Met Gln Val Ser Ser Leu Thr Tyr Glu Asp Ser Ala Val Tyr Tyr Cys
                 85                  90                  95
Ala Arg Asp Arg Ile Gly Tyr Trp Asp Phe Asp Val Trp Gly Thr Gly
                100                 105                 110
Thr Thr Val Thr Val Ser Ser
            115
```

<210> SEQ ID NO 40
<211> LENGTH: 106
<212> TYPE: PRT
<213> ORGANISM: Mus musculus

<400> SEQUENCE: 40

Asp Val Val Met Thr Gln Ser Gln Lys Phe Met Ser Thr Thr Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Thr Asn Met Gln Ser
65                  70                  75                  80

Glu Asp Leu Ala Asp Tyr Phe Cys Gln Gln Tyr Ser Ser Tyr Leu Thr
                85                  90                  95

Phe Gly Ala Gly Thr Lys Leu Asp Leu Lys
            100                 105

<210> SEQ ID NO 41
<211> LENGTH: 9
<212> TYPE: PRT
<213> ORGANISM: Mus musculus

<400> SEQUENCE: 41

Gly Phe Ser Leu Thr Thr Phe Gly Met
1               5

<210> SEQ ID NO 42
<211> LENGTH: 5
<212> TYPE: PRT
<213> ORGANISM: Mus musculus

<400> SEQUENCE: 42

Trp Trp Asn Asp Asp
1               5

<210> SEQ ID NO 43
<211> LENGTH: 15
<212> TYPE: PRT
<213> ORGANISM: Mus musculus

<400> SEQUENCE: 43

Thr Ile Tyr Tyr Gly Asn Tyr Leu Thr Phe Tyr Ala Met Glu His
1               5                   10                  15

<210> SEQ ID NO 44
<211> LENGTH: 16
<212> TYPE: PRT
<213> ORGANISM: Mus musculus

<400> SEQUENCE: 44

Arg Ser Ser Gln Asn Ile Val His Ser Asn Gly Asn Thr Tyr Leu Glu
1               5                   10                  15

<210> SEQ ID NO 45
<211> LENGTH: 7
<212> TYPE: PRT
<213> ORGANISM: Mus musculus

```
<400> SEQUENCE: 45

Lys Val Ser Asn Arg Phe Ser
1               5

<210> SEQ ID NO 46
<211> LENGTH: 9
<212> TYPE: PRT
<213> ORGANISM: Mus musculus

<400> SEQUENCE: 46

Phe Gln Gly Ser His Val Pro Pro Thr
1               5

<210> SEQ ID NO 47
<211> LENGTH: 9
<212> TYPE: PRT
<213> ORGANISM: Mus musculus

<400> SEQUENCE: 47

Gly Phe Ser Leu Ser Thr Phe Gly Met
1               5

<210> SEQ ID NO 48
<211> LENGTH: 5
<212> TYPE: PRT
<213> ORGANISM: Mus musculus

<400> SEQUENCE: 48

Trp Trp Asp Asp Asp
1               5

<210> SEQ ID NO 49
<211> LENGTH: 15
<212> TYPE: PRT
<213> ORGANISM: Mus musculus

<400> SEQUENCE: 49

Val Ile Tyr Tyr Gly Ser Arg Ser Ala Tyr Tyr Ser Met Asp Tyr
1               5                   10                  15

<210> SEQ ID NO 50
<211> LENGTH: 16
<212> TYPE: PRT
<213> ORGANISM: Mus musculus

<400> SEQUENCE: 50

Lys Ser Ser Gln Ser Ile Val His Ser Asn Gly His Thr Tyr Leu Glu
1               5                   10                  15

<210> SEQ ID NO 51
<211> LENGTH: 7
<212> TYPE: PRT
<213> ORGANISM: Mus musculus

<400> SEQUENCE: 51

Lys Val Ser Asn Arg Phe Ser
1               5

<210> SEQ ID NO 52
<211> LENGTH: 9
<212> TYPE: PRT
<213> ORGANISM: Mus musculus

<400> SEQUENCE: 52
```

```
Phe Gln Gly Ser His Val Pro Val Thr
1               5
```

<210> SEQ ID NO 53
<211> LENGTH: 10
<212> TYPE: PRT
<213> ORGANISM: Mus musculus

<400> SEQUENCE: 53

```
Gly Asp Thr Phe Thr Thr Tyr Asp Ile Thr
1               5                   10
```

<210> SEQ ID NO 54
<211> LENGTH: 6
<212> TYPE: PRT
<213> ORGANISM: Mus musculus

<400> SEQUENCE: 54

```
Tyr Pro Lys Asp Gly Arg
1               5
```

<210> SEQ ID NO 55
<211> LENGTH: 10
<212> TYPE: PRT
<213> ORGANISM: Mus musculus

<400> SEQUENCE: 55

```
Arg Gly Gln Phe Gly Pro Tyr Phe Asp His
1               5                   10
```

<210> SEQ ID NO 56
<211> LENGTH: 11
<212> TYPE: PRT
<213> ORGANISM: Mus musculus

<400> SEQUENCE: 56

```
Arg Ala Ser Asp His Ile Tyr Asn Trp Leu Ala
1               5                   10
```

<210> SEQ ID NO 57
<211> LENGTH: 7
<212> TYPE: PRT
<213> ORGANISM: Mus musculus

<400> SEQUENCE: 57

```
Gly Ala Thr Ser Leu Glu Thr
1               5
```

<210> SEQ ID NO 58
<211> LENGTH: 10
<212> TYPE: PRT
<213> ORGANISM: Mus musculus

<400> SEQUENCE: 58

```
Arg Gly Gln Phe Gly Pro Tyr Phe Asp His
1               5                   10
```

<210> SEQ ID NO 59
<211> LENGTH: 7
<212> TYPE: PRT
<213> ORGANISM: Mus musculus

<400> SEQUENCE: 59

```
Gly Phe Ser Phe Ser Thr Phe
1               5
```

```
<210> SEQ ID NO 60
<211> LENGTH: 6
<212> TYPE: PRT
<213> ORGANISM: Mus musculus

<400> SEQUENCE: 60

Ser Ser Gly Ser Tyr Ser
1               5

<210> SEQ ID NO 61
<211> LENGTH: 15
<212> TYPE: PRT
<213> ORGANISM: Mus musculus

<400> SEQUENCE: 61

Thr Arg Thr Arg Asp Ser Gly Ser Ser Pro His Tyr Phe Asp Tyr
1               5                   10                  15

<210> SEQ ID NO 62
<211> LENGTH: 15
<212> TYPE: PRT
<213> ORGANISM: Mus musculus

<400> SEQUENCE: 62

Arg Ala Ser Lys Ser Val Asp Ser Tyr Gly Ile Ser Phe Met Asn
1               5                   10                  15

<210> SEQ ID NO 63
<211> LENGTH: 7
<212> TYPE: PRT
<213> ORGANISM: Mus musculus

<400> SEQUENCE: 63

Gly Ala Ser Asn Arg Gly Ser
1               5

<210> SEQ ID NO 64
<211> LENGTH: 9
<212> TYPE: PRT
<213> ORGANISM: Mus musculus

<400> SEQUENCE: 64

Gln Gln Ser Lys Glu Gly Pro Phe Thr
1               5

<210> SEQ ID NO 65
<211> LENGTH: 7
<212> TYPE: PRT
<213> ORGANISM: Mus musculus

<400> SEQUENCE: 65

Gly Phe Thr Phe Ser Ser Tyr
1               5

<210> SEQ ID NO 66
<211> LENGTH: 6
<212> TYPE: PRT
<213> ORGANISM: Mus musculus

<400> SEQUENCE: 66

Ser Ser Ser Gly Arg Tyr
1               5
```

```
<210> SEQ ID NO 67
<211> LENGTH: 14
<212> TYPE: PRT
<213> ORGANISM: Mus musculus

<400> SEQUENCE: 67

Thr Gly Val Thr Thr Val Val Phe Thr Asp Tyr Phe Asp Tyr
1               5                   10

<210> SEQ ID NO 68
<211> LENGTH: 7
<212> TYPE: PRT
<213> ORGANISM: Mus musculus

<400> SEQUENCE: 68

Ser Gln Asp Ile Gly Asn Ser
1               5

<210> SEQ ID NO 69
<211> LENGTH: 5
<212> TYPE: PRT
<213> ORGANISM: Mus musculus

<400> SEQUENCE: 69

Ser Ser Leu Asp Ser
1               5

<210> SEQ ID NO 70
<211> LENGTH: 10
<212> TYPE: PRT
<213> ORGANISM: Mus musculus

<400> SEQUENCE: 70

Leu Gln Tyr Leu Ser Ser Pro Pro Thr Phe
1               5                   10

<210> SEQ ID NO 71
<211> LENGTH: 7
<212> TYPE: PRT
<213> ORGANISM: Mus musculus

<400> SEQUENCE: 71

Gly Phe Ser Leu Thr Thr His
1               5

<210> SEQ ID NO 72
<211> LENGTH: 5
<212> TYPE: PRT
<213> ORGANISM: Mus musculus

<400> SEQUENCE: 72

Trp Ser Gly Gly Asn
1               5

<210> SEQ ID NO 73
<211> LENGTH: 8
<212> TYPE: PRT
<213> ORGANISM: Mus musculus

<400> SEQUENCE: 73

Leu Leu Leu Pro Ala Met Asp Tyr
1               5

<210> SEQ ID NO 74
<211> LENGTH: 12
```

```
<212> TYPE: PRT
<213> ORGANISM: Mus musculus

<400> SEQUENCE: 74

Thr Ala Thr Ser Ser Val Ser Ser Thr Tyr Leu His
1               5                   10

<210> SEQ ID NO 75
<211> LENGTH: 7
<212> TYPE: PRT
<213> ORGANISM: Mus musculus

<400> SEQUENCE: 75

Ser Thr Ser Thr Leu Ala Ser
1               5

<210> SEQ ID NO 76
<211> LENGTH: 9
<212> TYPE: PRT
<213> ORGANISM: Mus musculus

<400> SEQUENCE: 76

His Gln Tyr Arg Arg Ser Pro Tyr Thr
1               5

<210> SEQ ID NO 77
<211> LENGTH: 7
<212> TYPE: PRT
<213> ORGANISM: Mus musculus

<400> SEQUENCE: 77

Gly Phe Thr Phe Arg Asn Tyr
1               5

<210> SEQ ID NO 78
<211> LENGTH: 6
<212> TYPE: PRT
<213> ORGANISM: Mus musculus

<400> SEQUENCE: 78

Ser Glu Ser Gly Asn Tyr
1               5

<210> SEQ ID NO 79
<211> LENGTH: 10
<212> TYPE: PRT
<213> ORGANISM: Mus musculus

<400> SEQUENCE: 79

Asp Asp Trp Glu Gly Arg Ala Met Asp Tyr
1               5                   10

<210> SEQ ID NO 80
<211> LENGTH: 11
<212> TYPE: PRT
<213> ORGANISM: Mus musculus

<400> SEQUENCE: 80

Arg Ala Ser Arg Asp Ile Gly Ser Ser Leu Asn
1               5                   10

<210> SEQ ID NO 81
<211> LENGTH: 7
<212> TYPE: PRT
<213> ORGANISM: Mus musculus
```

<400> SEQUENCE: 81

Ala Thr Ser Ser Leu Asp Ser
1               5

<210> SEQ ID NO 82
<211> LENGTH: 9
<212> TYPE: PRT
<213> ORGANISM: Mus musculus

<400> SEQUENCE: 82

Leu Gln Tyr Ala Ser Ser Pro Trp Thr
1               5

<210> SEQ ID NO 83
<211> LENGTH: 7
<212> TYPE: PRT
<213> ORGANISM: Mus musculus

<400> SEQUENCE: 83

Gly Tyr Thr Phe Thr Ser Tyr
1               5

<210> SEQ ID NO 84
<211> LENGTH: 6
<212> TYPE: PRT
<213> ORGANISM: Mus musculus

<400> SEQUENCE: 84

Asn Pro Ser Ser Gly Tyr
1               5

<210> SEQ ID NO 85
<211> LENGTH: 10
<212> TYPE: PRT
<213> ORGANISM: Mus musculus

<400> SEQUENCE: 85

Asp Arg Ile Gly Tyr Trp Asp Phe Asp Val
1               5                   10

<210> SEQ ID NO 86
<211> LENGTH: 11
<212> TYPE: PRT
<213> ORGANISM: Mus musculus

<400> SEQUENCE: 86

Lys Ala Ser Gln Asn Val Gly Thr Ala Val Ala
1               5                   10

<210> SEQ ID NO 87
<211> LENGTH: 7
<212> TYPE: PRT
<213> ORGANISM: Mus musculus

<400> SEQUENCE: 87

Ser Ala Ser Asn Arg Tyr Thr
1               5

<210> SEQ ID NO 88
<211> LENGTH: 8
<212> TYPE: PRT
<213> ORGANISM: Mus musculus

<400> SEQUENCE: 88

```
Gln Gln Tyr Ser Ser Tyr Leu Thr
1               5

<210> SEQ ID NO 89
<211> LENGTH: 130
<212> TYPE: PRT
<213> ORGANISM: Homo sapiens

<400> SEQUENCE: 89

Leu Cys Gln Gly Ser Asn Tyr Ser Thr Cys Ala Ser Cys Pro Ser Cys
1               5                   10                  15

Pro Asp Arg Trp Met Lys Tyr Gly Asn His Cys Tyr Tyr Phe Ser Val
            20                  25                  30

Glu Glu Lys Asp Trp Asn Ser Ser Leu Glu Phe Cys Leu Ala Arg Asp
        35                  40                  45

Ser His Leu Leu Val Ile Thr Asp Asn Gln Glu Met Ser Leu Leu Gln
    50                  55                  60

Val Phe Leu Ser Glu Ala Phe Cys Trp Ile Gly Leu Arg Asn Asn Ser
65                  70                  75                  80

Gly Trp Arg Trp Glu Asp Gly Ser Pro Leu Asn Phe Ser Arg Ile Ser
                85                  90                  95

Ser Asn Ser Phe Val Gln Thr Cys Gly Ala Ile Asn Lys Asn Gly Leu
            100                 105                 110

Gln Ala Ser Ser Cys Glu Val Pro Leu His Trp Val Cys Lys Lys Val
        115                 120                 125

Arg Leu
    130

<210> SEQ ID NO 90
<211> LENGTH: 130
<212> TYPE: PRT
<213> ORGANISM: Macaca fascicularis

<400> SEQUENCE: 90

Leu Cys Gln Gly Ser Lys Tyr Ser Thr Cys Ala Ser Cys Pro Ser Cys
1               5                   10                  15

Pro Asp His Trp Met Lys Tyr Gly Asn His Cys Tyr Tyr Phe Ser Val
            20                  25                  30

Glu Lys Lys Asp Trp Ile Ser Ser Leu Glu Phe Cys Leu Ala Arg Asp
        35                  40                  45

Ser His Leu Leu Met Ile Thr Asp Lys Gln Glu Met Ser Leu Leu Gln
    50                  55                  60

Asp Phe Leu Ser Glu Ala Phe His Trp Val Gly Leu Arg Asn Asn Ser
65                  70                  75                  80

Gly Trp Arg Trp Glu Asp Gly Ser Pro Leu Asn Phe Ser Arg Ile Tyr
                85                  90                  95

Ser Asn Ser Leu Val Gln Thr Cys Gly Ala Ile Asn Lys Asn Ser Leu
            100                 105                 110

Gln Ala Ser Ser Cys Glu Val Ser Leu Gln Trp Val Cys Lys Lys Val
        115                 120                 125

Ser Pro
    130

<210> SEQ ID NO 91
<211> LENGTH: 728
<212> TYPE: PRT
<213> ORGANISM: Homo sapiens
```

<400> SEQUENCE: 91

```
Asp Trp Val Ile Pro Pro Ile Ser Cys Pro Glu Asn Glu Lys Gly Pro
1               5                   10                  15

Phe Pro Lys Asn Leu Val Gln Ile Lys Ser Asn Lys Asp Lys Glu Gly
            20                  25                  30

Lys Val Phe Tyr Ser Ile Thr Gly Gln Gly Ala Asp Thr Pro Pro Val
        35                  40                  45

Gly Val Phe Ile Ile Glu Arg Glu Thr Gly Trp Leu Lys Val Thr Glu
    50                  55                  60

Pro Leu Asp Arg Glu Arg Ile Ala Thr Tyr Thr Leu Phe Ser His Ala
65                  70                  75                  80

Val Ser Ser Asn Gly Asn Ala Val Glu Asp Pro Met Glu Ile Leu Ile
                85                  90                  95

Thr Val Thr Asp Gln Asn Asp Asn Lys Pro Glu Phe Thr Gln Glu Val
            100                 105                 110

Phe Lys Gly Ser Val Met Glu Gly Ala Leu Pro Gly Thr Ser Val Met
        115                 120                 125

Glu Val Thr Ala Thr Asp Ala Asp Asp Val Asn Thr Tyr Asn Ala
130                 135                 140

Ala Ile Ala Tyr Thr Ile Leu Ser Gln Asp Pro Glu Leu Pro Asp Lys
145                 150                 155                 160

Asn Met Phe Thr Ile Asn Arg Asn Thr Gly Val Ile Ser Val Val Thr
                165                 170                 175

Thr Gly Leu Asp Arg Glu Ser Phe Pro Thr Tyr Thr Leu Val Val Gln
            180                 185                 190

Ala Ala Asp Leu Gln Gly Glu Gly Leu Ser Thr Thr Ala Thr Ala Val
        195                 200                 205

Ile Thr Val Thr Asp Thr Asn Asp Asn Pro Pro Ile Phe Asn Pro Thr
210                 215                 220

Thr Tyr Lys Gly Gln Val Pro Glu Asn Glu Ala Asn Val Val Ile Thr
225                 230                 235                 240

Thr Leu Lys Val Thr Asp Ala Asp Ala Pro Asn Thr Pro Ala Trp Glu
                245                 250                 255

Ala Val Tyr Thr Ile Leu Asn Asp Asp Gly Gly Gln Phe Val Val Thr
            260                 265                 270

Thr Asn Pro Val Asn Asn Asp Gly Ile Leu Lys Thr Ala Lys Gly Leu
        275                 280                 285

Asp Phe Glu Ala Lys Gln Gln Tyr Ile Leu His Val Ala Val Thr Asn
290                 295                 300

Val Val Pro Phe Glu Val Ser Leu Thr Thr Ser Thr Ala Thr Val Thr
305                 310                 315                 320

Val Asp Val Leu Asp Val Asn Glu Ala Pro Ile Phe Val Pro Pro Glu
                325                 330                 335

Lys Arg Val Glu Val Ser Glu Asp Phe Gly Val Gly Gln Glu Ile Thr
            340                 345                 350

Ser Tyr Thr Ala Gln Glu Pro Asp Thr Phe Met Glu Gln Lys Ile Thr
        355                 360                 365

Tyr Arg Ile Trp Arg Asp Thr Ala Asn Trp Leu Glu Ile Asn Pro Asp
370                 375                 380

Thr Gly Ala Ile Ser Thr Arg Ala Glu Leu Asp Arg Glu Asp Phe Glu
385                 390                 395                 400

His Val Lys Asn Ser Thr Tyr Thr Ala Leu Ile Ile Ala Thr Asp Asn
```

```
            405                 410                 415
Gly Ser Pro Val Ala Thr Gly Thr Gly Thr Leu Leu Ile Leu Ser
            420                 425                 430

Asp Val Asn Asp Asn Ala Pro Ile Pro Glu Pro Arg Thr Ile Phe Phe
            435                 440                 445

Cys Glu Arg Asn Pro Lys Pro Gln Val Ile Asn Ile Ile Asp Ala Asp
450                 455                 460

Leu Pro Pro Asn Thr Ser Pro Phe Thr Ala Glu Leu Thr His Gly Ala
465                 470                 475                 480

Ser Ala Asn Trp Thr Ile Gln Tyr Asn Asp Pro Thr Gln Ser Ile
                485                 490                 495

Ile Leu Lys Pro Lys Met Ala Leu Glu Val Gly Asp Tyr Lys Ile Asn
            500                 505                 510

Leu Lys Leu Met Asp Asn Gln Asn Lys Asp Gln Val Thr Thr Leu Glu
            515                 520                 525

Val Ser Val Cys Asp Cys Glu Gly Ala Ala Gly Val Cys Arg Lys Ala
530                 535                 540

Gln Pro Val Glu Ala Gly Leu Gln Ile Pro Ala Ile Leu Gly Ile Leu
545                 550                 555                 560

Gly Gly Ile Leu Ala Leu Leu Ile Leu Ile Leu Leu Leu Leu Leu Phe
                565                 570                 575

Leu Arg Arg Arg Ala Val Val Lys Glu Pro Leu Leu Pro Pro Glu Asp
            580                 585                 590

Asp Thr Arg Asp Asn Val Tyr Tyr Tyr Asp Glu Glu Gly Gly Gly Glu
            595                 600                 605

Glu Asp Gln Asp Phe Asp Leu Ser Gln Leu His Arg Gly Leu Asp Ala
610                 615                 620

Arg Pro Glu Val Thr Arg Asn Asp Val Ala Pro Thr Leu Met Ser Val
625                 630                 635                 640

Pro Arg Tyr Leu Pro Arg Pro Ala Asn Pro Asp Glu Ile Gly Asn Phe
                645                 650                 655

Ile Asp Glu Asn Leu Lys Ala Ala Asp Thr Asp Pro Thr Ala Pro Pro
            660                 665                 670

Tyr Asp Ser Leu Leu Val Phe Asp Tyr Glu Gly Ser Gly Ser Glu Ala
            675                 680                 685

Ala Ser Leu Ser Ser Leu Asn Ser Ser Glu Ser Asp Lys Asp Gln Asp
690                 695                 700

Tyr Asp Tyr Leu Asn Glu Trp Gly Asn Arg Phe Lys Lys Leu Ala Asp
705                 710                 715                 720

Met Tyr Gly Gly Gly Glu Asp Asp
                725
```